US010385120B2

(12) United States Patent
Leonetti et al.

(10) Patent No.: US 10,385,120 B2
(45) Date of Patent: *Aug. 20, 2019

(54) MOLECULAR COMPLEX FOR TARGETING ANTIGENS TOWARDS CELLS COMPRISING ANTIGENS AND USES THEREOF FOR VACCINATION

(75) Inventors: Michel Leonetti, Nozay (FR); Alexandra Savatier, Etampes (FR); Adeline Gadzinski, Villeparisis (FR); Jean-Claude Boulain, Palaiseau (FR)

(73) Assignee: Commissariat a l'Energie Atomique, Paris (FR)

( * ) Notice: Subject to any disclaimer, the term of this patent is extended or adjusted under 35 U.S.C. 154(b) by 694 days.

This patent is subject to a terminal disclaimer.

(21) Appl. No.: 13/576,083

(22) PCT Filed: Feb. 1, 2011

(86) PCT No.: PCT/IB2011/050437
§ 371 (c)(1),
(2), (4) Date: Sep. 27, 2012

(87) PCT Pub. No.: WO2011/092675
PCT Pub. Date: Aug. 4, 2011

(65) Prior Publication Data
US 2013/0195908 A1 Aug. 1, 2013

(30) Foreign Application Priority Data

Feb. 1, 2010 (FR) .................................... 10 00392

(51) Int. Cl.

| C07K 1/00 | (2006.01) |
|---|---|
| C07K 14/00 | (2006.01) |
| C07K 16/00 | (2006.01) |
| C07K 17/00 | (2006.01) |
| C07K 16/18 | (2006.01) |
| A61K 39/39 | (2006.01) |
| C07K 16/28 | (2006.01) |
| A61K 47/64 | (2017.01) |
| A61K 47/68 | (2017.01) |
| A61K 39/00 | (2006.01) |

(52) U.S. Cl.
CPC .............. *C07K 16/18* (2013.01); *A61K 39/39* (2013.01); *A61K 47/64* (2017.08); *A61K 47/6415* (2017.08); *A61K 47/6811* (2017.08); *C07K 16/2833* (2013.01); *A61K 2039/605* (2013.01)

(58) Field of Classification Search
None
See application file for complete search history.

(56) References Cited

U.S. PATENT DOCUMENTS

2004/0249126 A1* 12/2004 Celis .................. C07K 14/4748
530/350
2004/0258688 A1 12/2004 Hawiger et al.

FOREIGN PATENT DOCUMENTS

| WO | 1998/034956 | 8/1998 | |
|---|---|---|---|
| WO | 2003/084467 | 10/2003 | |
| WO | 2005/097179 | 10/2005 | |
| WO | 2007/015704 | 2/2007 | |
| WO | WO-2007076904 A1 * | 7/2007 | ............. C07K 14/79 |

OTHER PUBLICATIONS

Nilsson et al., 1987, Prot. Engineer. vol. 1: 107-113.*
Madshus et al., 1991, J. Biol. Chem. vol. 266: 17446-17453.*
Raju et al., 1995, Eur. J. Immunol. vol. 25: 3207-3214.*
Greenfield et al., 1983, PNAS, vol. 80: 6853-6857.*
Kerscher eta l., 2013, Int. Immunol. vol. 25: 271-277.*
Lee et al., 2004, Appl. Environ, Microbiol., vol. 70: 4569-4574.*
Aminian et al., 2007, Prot. Exp. PUrif. vol. 51: 170-178.*
Zhao et al., 2005, Vaccine, vol. 23: 5082-5090.*
Lobeck et al., 1998, Infect. Immun. vol. 66: 418-423.*
Lowenadler et al., 1992, Mol. Immunol. vol. 29: 1185-1190.*
Renz et al., 1993, J. Immunol. vol. 151: 7206-7213.*
Clark et al., 2006, Trends Biotech. vol. 24: 212-218.*
Yang, Engineered Lentivector Targeting of Dendritic Cells for in Vivo Immunization, Nature Biotechnology, 26, pp. 326-334, 2008.
Wang, HBcAg18-27 Epitope Fused to HIV-Tat49-57 Adjuvanted with CpG ODN Induces Immunotherapeutic Effects in Transgenic Mice, Immunology Letters, 127, pp. 143-149, 2010.
Gadzinski, P02-01. Elicitation of a Humoral Immune Response Towards Non-Immunogenic Peptides Using the Transcriptional Transactivator of HIV-1, Retrovirology, 6, p. 6, 2009.
Turbant, Cynomolgus Macaques Immunized with Two HIV-1 Tat Stabilized Proteins Raise Strong and Long-Lasting Immune Responses With a Pattern of Th1/Th2 Response Differing from that in Mice, Vaccine, 27, pp. 5349-5356, 2009.
Lecoq, Increasing the Humoral Immunogenic Properties of the HIV-1 Tat Protein Using a Ligand-Stabilizing Strategy, Vaccine, 26, pp. 2615-2626, 2008.
Kittiworakarn, HIV-1 Tat Raises an Adjuvant-Free Humoral Immune Response Controlled by its Core Region and Its Ability to Form Cysteine-Mediated Oligomers, Journal of Biological Chemistry, 281, pp. 3105-3115, 2006.
Watson, Interaction of the Transactivating Protein HIV-1 Tat with Sulphated Polysaccharides, Biochemical Pharmacology, 57, pp. 775-783, 1999.

(Continued)

*Primary Examiner* — Amy E Juedes

(74) *Attorney, Agent, or Firm* — Morgan, Lewis & Bockius LLP

(57) ABSTRACT

The invention relates to a molecular complex for targeting the antigen towards cells comprising antigens, including at least one antigen associated with at least two ligands of surface molecules of cells comprising antigens, said complex including at least one first ligand of a sulphated sugar of the glycosaminoglycan family and a second ligand of a specific surface molecule of cells comprising antigens, and said first ligand being covalently bonded with said antigen and/or said second ligand.

6 Claims, 17 Drawing Sheets

Figure 1:
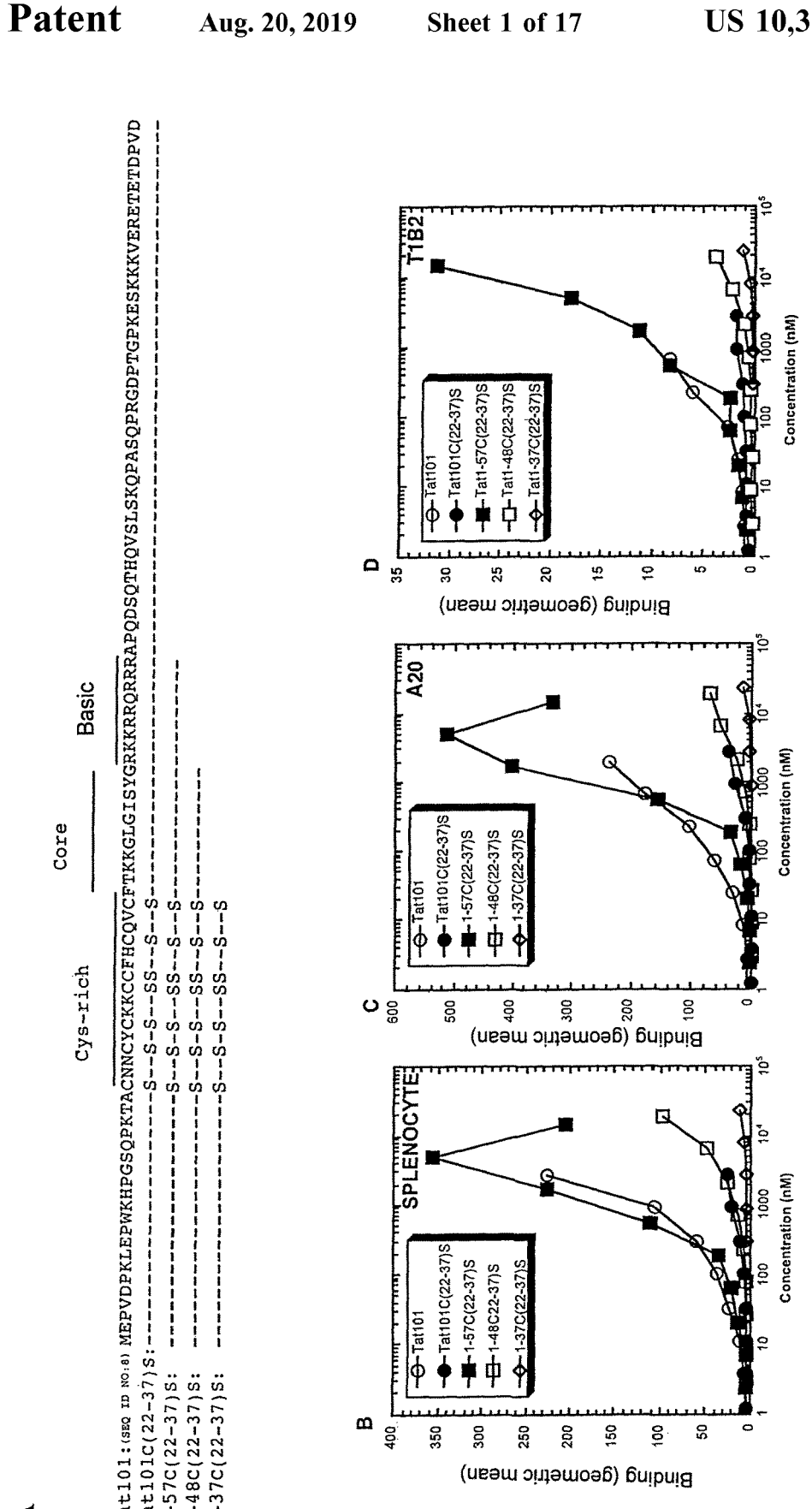

Specification includes a Sequence Listing.

(56) References Cited

OTHER PUBLICATIONS

Leonetti, Presentation of Antigen in Immune Complexes is Boosted by Soluble Bacterial Immunoglobulin Binding Proteins, Journal of Experimental Medicine, 189, pp. 1217-1228, 1999.

Leonetti, Increasing Immunogenicity of Antigens Fused to Ig-Binding Proteins by Cell Surface Targeting, Journal of Immunology, 160, pp. 3820-3827, 1998.

Mitsui, Polyarginine-Mediated Protein Delivery to Dendritic Cells Presents Antigen More efficiently onto MHC Class I and Class II and Elicits Superior Anitiumor Immunity, Journal of Investigative Dermatology, 126, pp. 1804-1812, 2006.

Krishnamachari, Innovative Strategies for Co-Delivering Antigens and CpG Oligonucleotides, Advanced Drug Delivery Reviews, 61, pp. 205-217, 2009.

Rudolf, Potent Costimulation of Human CD8 T Cells by Anti-4-1BB and Anti-CD28 on Synthetic Artificial Antigen Presenting Cells, Cancer Immunology Immunotherapy, 57, pp. 175-183, 2007.

Bozzacco, DEC-205 Receptor on Dendritic Cells Medicates Presentation of HIV Gag Protein to CD8+ T Cells in a Spectrum of Human MHC I Haplotypes, Proceedings of the National Academy of Sciences of the United States of America, 104, pp. 1289-1294, 2007.

\* cited by examiner

SEQUENCE LISTING

<160> NUMBER OF SEQ ID NOS: 14

<210> SEQ ID NO 1
<211> LENGTH: 9
<212> TYPE: PRT
<213> ORGANISM: artificial sequence
<220> FEATURE:
<223> OTHER INFORMATION: HIV-1 Tat 49-57 peptide (basic region)

<400> SEQUENCE: 1

Arg Lys Lys Arg Arg Gln Arg Arg Arg
1               5

<210> SEQ ID NO 2
<211> LENGTH: 16
<212> TYPE: PRT
<213> ORGANISM: artificial sequence
<220> FEATURE:
<223> OTHER INFORMATION: penetratin peptide : Antennapedia protein
      homeodomain peptide 43-58

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 116
<212> TYPE: PRT
<213> ORGANISM: artificial sequence
<220> FEATURE:
<223> OTHER INFORMATION: ZZ derivative of S.aureus Protein A BB domain

<400> SEQUENCE: 3

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
    50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys
        115

<210> SEQ ID NO 4
<211> LENGTH: 116
<212> TYPE: PRT
<213> ORGANISM: artificial sequence
<220> FEATURE:
<223> OTHER INFORMATION: S. aureus Protein A BB domain

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

```
Ser Leu Lys Asp Asp Pro Ser Gln Ser Ala Asn Leu Leu Ala Glu Ala
            35                  40                  45

Lys Lys Leu Asn Asp Ala Gln Ala Pro Lys Ala Asp Asn Lys Phe Asn
 50                  55                  60

Lys Glu Gln Gln Asn Ala Phe Tyr Glu Ile Leu His Leu Pro Asn Leu
 65                  70                  75                  80

Asn Glu Glu Gln Arg Asn Gly Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys
        115

<210> SEQ ID NO 5
<211> LENGTH: 11
<212> TYPE: PRT
<213> ORGANISM: artificial sequence
<220> FEATURE:
<223> OTHER INFORMATION: HIV-1 Tat 38-48 peptide (core region)

<400> SEQUENCE: 5

Phe Thr Lys Lys Gly Leu Gly Ile Ser Tyr Gly
 1               5                  10

<210> SEQ ID NO 6
<211> LENGTH: 154
<212> TYPE: PRT
<213> ORGANISM: artificial sequence
<220> FEATURE:
<223> OTHER INFORMATION: Diphteria Toxin R domain named DTR or DTR-BD

<400> SEQUENCE: 6

Pro Gly His Lys Thr Gln Pro Phe Leu His Asp Gly Tyr Ala Val Ser
 1               5                  10                  15

Trp Asn Thr Val Glu Asp Ser Ile Ile Arg Thr Gly Phe Gln Gly Glu
                20                  25                  30

Ser Gly His Asp Ile Lys Ile Thr Ala Glu Asn Thr Pro Leu Pro Ile
            35                  40                  45

Ala Gly Val Leu Leu Pro Thr Ile Pro Gly Lys Leu Asp Val Asn Lys
 50                  55                  60

Ser Lys Thr His Ile Ser Val Asn Gly Arg Lys Ile Arg Met Arg Cys
 65                  70                  75                  80

Arg Ala Ile Asp Gly Asp Val Thr Phe Cys Arg Pro Lys Ser Pro Val
                85                  90                  95

Tyr Val Gly Asn Gly Val His Ala Asn Leu His Val Ala Phe His Arg
            100                 105                 110

Ser Ser Ser Glu Lys Ile His Ser Asn Glu Ile Ser Ser Asp Ser Ile
        115                 120                 125

Gly Val Leu Gly Tyr Gln Lys Thr Val Asp His Thr Lys Val Asn Ser
    130                 135                 140

Lys Leu Ser Leu Phe Phe Glu Ile Lys Ser
145                 150

<210> SEQ ID NO 7
<211> LENGTH: 21
<212> TYPE: PRT
<213> ORGANISM: artificial sequence
<220> FEATURE:
<223> OTHER INFORMATION: HIV-1 Tat 37-57 peptide (core and basic
      regions)
```

-continued

<400> SEQUENCE: 7

Cys Phe Thr Lys Lys Gly Leu Gly Ile Ser Tyr Gly Arg Lys Lys Arg
1               5                   10                  15

Arg Gln Arg Arg Arg
            20

<210> SEQ ID NO 8
<211> LENGTH: 101
<212> TYPE: PRT
<213> ORGANISM: artificial sequence
<220> FEATURE:
<223> OTHER INFORMATION: HIV-1 Tat consensus sequence

<400> SEQUENCE: 8

Met Glu Pro Val Asp Pro Lys Leu Glu Pro Trp Lys His Pro Gly Ser
1               5                   10                  15

Gln Pro Lys Thr Ala Cys Asn Asn Cys Tyr Cys Lys Lys Cys Cys Phe
                20                  25                  30

His Cys Gln Val Cys Phe Thr Lys Lys Gly Leu Gly Ile Ser Tyr Gly
            35                  40                  45

Arg Lys Lys Arg Arg Gln Arg Arg Arg Ala Pro Gln Asp Ser Gln Thr
50                  55                  60

His Gln Val Ser Leu Ser Lys Gln Pro Ala Ser Gln Pro Arg Gly Asp
65                  70                  75                  80

Pro Thr Gly Pro Lys Glu Ser Lys Lys Val Glu Arg Glu Thr Glu
                85                  90                  95

Thr Asp Pro Val Asp
            100

<210> SEQ ID NO 9
<211> LENGTH: 60
<212> TYPE: PRT
<213> ORGANISM: Naja nigricollis

<400> SEQUENCE: 9

Leu Lys Cys Asn Gln Leu Ile Pro Pro Phe Trp Lys Thr Cys Pro Lys
1               5                   10                  15

Gly Lys Asn Leu Cys Tyr Lys Met Thr Met Arg Ala Ala Pro Met Val
                20                  25                  30

Pro Val Lys Arg Gly Cys Ile Asp Val Cys Pro Lys Ser Ser Leu Leu
            35                  40                  45

Ile Lys Tyr Met Cys Cys Asn Thr Asp Lys Cys Asn
    50                  55                  60

<210> SEQ ID NO 10
<211> LENGTH: 8
<212> TYPE: PRT
<213> ORGANISM: artificial sequence
<220> FEATURE:
<223> OTHER INFORMATION: ovalbulmine T CD8+ epitope

<400> SEQUENCE: 10

Ser Ile Ile Asn Phe Glu Lys Leu
1               5

<210> SEQ ID NO 11
<211> LENGTH: 5
<212> TYPE: PRT
<213> ORGANISM: artificial sequence
<220> FEATURE:

-continued

```
<223> OTHER INFORMATION: ovalbuline T CD8+ epitope flanking sequence

<400> SEQUENCE: 11

Leu Glu Gln Leu Glu
1               5

<210> SEQ ID NO 12
<211> LENGTH: 5
<212> TYPE: PRT
<213> ORGANISM: artificial sequence
<220> FEATURE:
<223> OTHER INFORMATION: ovalbuline T CD8+ epitope flanking sequence

<400> SEQUENCE: 12

Thr Glu Trp Thr Ser
1               5

<210> SEQ ID NO 13
<211> LENGTH: 13
<212> TYPE: PRT
<213> ORGANISM: artificial sequence
<220> FEATURE:
<223> OTHER INFORMATION: ovalbumine T CD4+ epitope

<400> SEQUENCE: 13

Ser Tyr Lys Lys Val Trp Arg Asp His Arg Gly Thr Ile
1               5                   10

<210> SEQ ID NO 14
<211> LENGTH: 11
<212> TYPE: PRT
<213> ORGANISM: artificial sequence
<220> FEATURE:
<223> OTHER INFORMATION: HIV-1 Tat 47-57 peptide (basic region)

<400> SEQUENCE: 14

Tyr Gly Arg Lys Lys Arg Arg Gln Arg Arg Arg
1               5                   10
```

MOLECULAR COMPLEX FOR TARGETING ANTIGENS TOWARDS CELLS COMPRISING ANTIGENS AND USES THEREOF FOR VACCINATION

RELATED APPLICATIONS

The present application is a U.S. National Phase Application of International Application No. PCT IB2011/050437 (filed Feb. 1, 2011) which claims priority to French Application No. 1000392 (filed Feb. 1, 2010) which are hereby incorporated by reference in their entirety.

Sequence Listing Submission via EFS-Web

A computer readable text file, entitled "045636-5201_SequenceListing.txt," created on or about Jun. 8, 2012, with a file size of about 8 kb contains the sequence listing for this application and is hereby incorporated by reference in its entirety.

The present invention relates to a novel molecular complex for targeting antigens to antigen-presenting cells, comprising at least one antigen associated with at least two ligands of molecules expressed at the surface of antigen-presenting cells, including a ligand of a sulfated sugar of the glycosaminoglycan family. The present invention also relates to compositions containing said complex and to the use thereof as a vaccine.

When vaccines are developed, it is sought to induce strong immune responses since the vaccinating efficacy is, most often, correlated with the level of immune response previously generated. The ability to induce high immune responses has three additional advantages. Firstly, it can make it possible to limit the number of vaccinations to be carried out in order to achieve the required level of immunity. Secondly, it can make it possible to do without adjuvants and thus to avoid the risks of toxicity associated with the use thereof. Thirdly, it can make it possible to reduce the doses of vaccine injected and thus result in a larger number of vaccine doses being obtained for the same level of production. The many advantages provided by the ability to induce strong immune responses have therefore led many research groups to attempt to develop approaches having the aim of increasing the immunogenicity of the antigens to be injected in animals or in humans.

The immune response is initiated at the level of specialized presenting cells, the antigen-presenting cells (APCs) which include dendritic cells (DCs). DCs express a large variety of surface molecules, including the major histocompatibility complex (MHC) molecules which bind antigen fragments and present them to T lymphocytes. These peptide/MHC molecule complexes are recognized by the receptors expressed at the surface of T lymphocytes, which thus become activated and contribute to the immune response. Two types of MHC molecules can be distinguished: MHC class I molecules which present the antigen to CD8+ T cells and make it possible to induce the cytotoxic T response, and MHC class II molecules which present the antigen to CD4+ T cells and thus contribute to triggering and maintaining the humoral response. The antigens (Ags) provided exogenously to the APCs are processed so as to be generally associated with MHC class II molecules. However, APCs and, in particular, DCs are also capable of processing exogenous antigens and of presenting them in association with MHC class I molecules according to a "cross-presentation" process (Sigal et al., Nature, 1999, 398, 77-80; Rock, K. L., Nature Immunology, 2003, 4, 941-943; Kasturi, S. P. and Pulendran, B., Nature Immunology, 2008, 9, 461-463). Thus, MHC class II molecule-restricted antigen presentation and MHC class I molecule-restricted cross-presentation play a central role in initiating and amplifying humoral and cytotoxic immune responses.

As a result, a large number of approaches having the object of increasing antigen immunogenicity are based on improving the effectiveness of antigen presentation and cross-presentation mechanisms. Since the effectiveness of the two presentation mechanisms depends on the prior capture of exogenous Ags by APCs, these approaches are mainly based on the targeting of said Ags to the APCs. For targeting Ags, it is sought to selectively reach the APCs since interaction with other cells lacking a presentation capacity could result in a dilution of the amount of Ag available for the APCs and thus to a decrease in the immune response. In order to achieve this selectivity, surface molecules expressed essentially on APCs are targeted. The surface receptors of APCs which were successfully used as a target for increasing antigen immunogenicity are mainly: MHC molecules, in particular MHC class II molecules; integrins (CD11c, MAC1), C-type lectin receptors (mannose receptor (CD206), DEC-205 (CD205), DC-SIGN (CD209), LOX1, Dectin-1 (beta-glucan receptor), Dectin-2, Clec9A, Clec12A, DCIR2, FIRE, CIRE), surface immunoglobulins or membrane immunoglobulins, receptors for the constant region of immunoglobulins (FcR) and in particular of IgGs (FcγR, FcgammaR: FcγRI (CD64), FcγRII (CD32), FcγRIII (CD16)), the TNF receptors superfamily (CD40) and complement receptors (receptor for component C5a or C3d (CD21); for a review see, in particular, Keler et al., Oncogene, 2007, 26, 3758-3767; Tacken et al., Nature Reviews, Immunology, 2007, 7, 790-; Shortman et al., Exp. Mol. Med., 2009, 41, 61-66). The targeting of other APC receptors, in particular the heat shock protein receptor (HSR), such as the CD91 molecule (International Application WO 03/084467), and the interferon-gamma receptor (application US 2007/0031445), has also been reported. The targeting of the antigen to the APCs is carried out with an antigen associated with a ligand of these APC surface molecules.

This ligand is generally a monoclonal antibody (Ab) specific for these APC surface molecules, or a derived fragment (F(ab')$_2$, scFv). In this type of vaccine, called antibody-targeted vaccine or ATV, the Ag is generally bound to the Ab at a site distinct from the paratope, most commonly at the C-terminal end of the heavy chain (constant region) of a whole antibody or of one of the variable regions (VH or VL) of a single-chain antibody fragment (scFv). The coupling of the Ag to the antibody is, either a covalent coupling such as a chemical coupling or a genetic fusion (fusion protein), or a noncovalent coupling by means of streptavidin-biotin complexes or complexes between the Ab and the Ag coupled or fused to a protein (protein A) or a protein fragment which binds immunoglobulins. Antibody-targeted vaccines are in particular described in U.S. Pat. No. 6,365,161 (anti-FcR Ab), PCT International Applications WO 99/29344, WO 00/00156 (anti-MHC II Ab, anti-CD11c Ab), WO 01/64254 (anti-FcR Ab and polyclonal immunoglobulin fragment Fc), WO 2008/097866 (anti-DCIR Ab), WO 2008/103953 (anti-LOX1 Ab), application US 2004/0258688 (anti-DEC-205 Ab), Bozzacco et al., PNAS, 2007, 104, 1289-1294 (anti-DEC-205 Ab), Tacken et al., J. Immunol., 2008, 180, 7687-7696 (anti-DC-SIGN Ab), application FR 2 759 296 and Léonetti et al., J. Immunol., 1998, 160, 3820-3827 (anti-MHC II Ab, anti-IgG-F(ab')$_2$ Ab, anti-IgM Ab). These antibody-targeted vaccines have shown that the targeting makes it possible to considerably increase capture of the Ag by the APCs and its endocytosis into the processing compartments, thereby making it possible to increase the antigen presentation to T cells and therefore the ability of the Ag to stimulate T cells and to induce the immune response. Ligand-mediated targeting to APCs therefore represents an approach of choice for increasing the immunogenicity of molecules of vaccination interest. These approaches carried out in the presence or in the absence of adjuvant have resulted in promising results. It has in particular been shown that the MHC class I-restricted CTL response and also the MHC class II-restricted T-helper response can be induced more effectively. These immune responses make it possible to envision an improvement in the defenses with respect to infectious diseases and cancers. However, no vaccine has, to date, been marketed on the basis of these approaches, which suggests that the ability to induce protective immune responses remains insufficient.

Alternatively, the ligand is a polyclonal antibody specific for the antigen, the vaccine then consisting of Ab/Ag complexes (immune complexes, ICs), optionally associated with a protein which binds immunoglobulins (Igs), such as *S. aureus* protein A (Léonetti et al., J. Exp. Med., 1999, 189, 1217-1228). Various studies have shown that antibodies specific for a given antigen can increase the presentation to T-helper cells, by delivering the immune complexes to Fc receptors for IgGs (FcγR or Fcgamma receptor) expressed at the surface of APCs (Manca et al., J. Exp. Med., 1991, 173, 37-48; Rouas-Freiss et al., Eur. J. Immunol., 1993, 23, 3335-3344; Manca et al., J. Immunol., 1988, 140, 2393-2398; Exposito et al., J. Immunol., 1995, 155, 1725-1736). Furthermore, it has been shown that immune complexes bound to FcγRs on dendritic cells are presented by the MHC class I molecules at the surface of these cells (Regnault et al., J. Exp. Med., 1999, 189, 371-380). However, the approaches targeted on FcγRs could provide relatively limited effects owing to the expression of FcγRs at the surface of cells not specialized in Ag presentation and because the Fcgamma II receptor has an isoform which inhibits the presentation of immune complexes (Amigorena et al., Science, 1992, 256, 1808-1812).

Other APC-specific ligands have also been described. Mention may in particular be made of a family of *Staphylococcus aureus* exoproteins exhibiting homology with superantigens (SSL proteins for staphylococcal superantigen-like exoproteins; PCT International Application WO 2005/092918), proteins and protein fragments which bind Igs, such as *Staphylococcus aureus* protein A and its ZZ derivative (Lobeck et al., Inf. Immunity, 1998, 66, 418-423; Léonetti et al., J; Immunol., 1998, 160, 3820-3827), a targeting sequence derived from the gp96 protein which binds CD91 (International Application WO 03/084467), recombinant human monoclonal Abs which bind dendritic cells, selected from a phage library (application US 2005/0037001), particles (type 0 red blood cell ghosts) comprising an antigen and ATP, coated with an APC ligand (IgG, complement component C3b or Cbi, maleic anhydride, oxidized lipid, sugar or polyanion; PCT International Application WO 02/20042), C5a-agonist or interferon-gamma-analog peptides (application US 2007/0031445).

The surface of the cells is coated with glycolipids and glycoproteins (glycocalyx) such as proteoglycans, or glycoproteins comprising one or more unbranched glycosaminoglycan (GAG) chains. The proteoglycans can be either transported out of the cell by exocytosis, in which case they integrate into the extracellular matrix, in the form of chondroitin sulfate, keratan sulfate, heparan sulfate, or dermatan sulfate, or become part of the make-up of the plasma membrane or of the glycocalyx, in which case they play a role in cell-matrix relationships. Heparan sulfate proteoglycans are ubiquitous molecules present at the surface of mammalian cells and in extracellular matrices (Dreyfuss et al., Annuals of the Brazilian Academy of Sciences, 2009, 81, 409-429). These molecules play a central role in many biological processes (cell proliferation, cell adhesion, inflammation, coagulation, cell penetration of pathogenic microorganisms, in particular viruses and parasites). Their properties are mainly mediated via the saccharide portion: heparan sulfate.

Generally, the targeting of molecules which are not selectively expressed at the surface of APCs is not considered to be a particularly effective approach since, in vivo, it leads to dissemination of the Ag on a large number of cells that are not specialized in the induction of the immune response, thereby resulting in a decrease in the amount of Ag available for the APCs. This nonspecific targeting is considered to be a drawback that it is sought to eliminate for in vivo vaccination applications.

For example, recombinant lentiviral vectors pseudotyped with the Sindbis virus envelope glycoprotein (SVG), which target the DC-SIGN surface molecule of DCs, are used in vaccination. However, such vectors do not allow selective targeting of DCs due to the fact that the SVG protein binds heparan sulfates (HS), which are ubiquitous surface molecules, expressed on numerous mammalian cell types. Thus, in order to improve the targeting of these vaccine vectors, the SVG protein has been mutated so that it loses its HS-binding capacity (Yang et al., Nat. Biotechnol., 2008, 26, 326-334).

An alternative approach for delivering an antigen to APCs consists in bonding the antigen (covalent chemical coupling or fusion protein) to a cell penetrating peptide (CPP; Brooks et al., Biochimica et Biophysica Acta, 2009). These natural or synthetic peptides are either cationic peptides (rich in lysines and/or arginines), such as the peptides derived from the basic region of the HIV Tat protein (Tat 49-57: RKKRRQRRR (SEQ ID NO: 1)) and polyarginine peptides (R7 to R11), or basic/amphiphilic peptides, such as peptides derived from the homeodomain of the antennapedia protein (penetratin; fragment 43-58: RQIKIWFQNRRMKWKK (SEQ ID NO: 2)). These peptides are capable of being translocated through the plasma membrane of cells, via mechanisms of action which may or may not involve endocytosis mediated by a glycosaminoglycan (GAG) receptor, in particular heparan sulfates and chondroitin sulfates (Futaki et al., Biopolymers, Dec. 6, 2005). The CPPs initially used to improve the presentation of exogenous Ags (vaccine) by MHC I molecules (cross-presentation) and to induce a cytotoxic T response (PCT International Application WO 00/35949) are also capable of improving presentation of exogenous Ags by MHC II molecules and of stimulating CD4+ T lymphocytes (Schutze-Redelmeier et al., J. Immunol., 1996, 157, 650-655; Mitsui et al., Journal of Investigative Dermatology, 2006, 126, 1805-1812; Wang et al., Immunology Letters, 2009).

However, owing to the ubiquitous expression of GAGs, it is not possible to specifically target APCs. For this reason, the use of CPPs as a vaccine is considered to be an approach only for "ex vivo" vaccination (Tacken et al., J. Immunol., 2008, 180, 7687-7696). The first step carried out "ex vivo" consists of the isolation of dendritic cells from the patient, and then the loading of these cells with peptides. The second step carried out "in vivo" consists in injecting the Ag-loaded APCs in order to vaccinate. However, this two-step approach, which proves to be relatively effective for triggering protective immune response, remains laborious to set up and unsuitable for mass vaccination.

All these observations indicate that improving vaccination against infectious diseases or cancers requires increasing the immune response induced by candidate vaccines or by existing vaccines. The targeting of antigens to APCs, which represents an approach of choice for achieving this objective, should, however, be further optimized in order to be made even more effective. The development of optimized targeted approaches could make it possible: to induce greater protective effects making it possible to improve vaccine efficacy, to limit the number of boosters to be given, to reduce the doses injected and to do without adjuvant.

Although cell surface glycosaminoglycans such as heparan sulfates (HSs) do not appear to be particularly suitable targets for allowing the increase in a specific immune response, the inventors have discovered that the targeting thereof can allow a significant increase in, or even have a synergistic effect on, the immune response specific for immunogens which are associated with a ligand capable of selectively targeting APCs. In order to evaluate this aspect, the inventors have used two different constructs which each contain an Ag, an HS ligand and an APC receptor ligand. For these two types of constructs, the inventors have observed that the presence of double targeting provides a synergy of effect and thus makes it possible to increase the immune response, which is measured using an "in vitro" test of stimulation of T cells specific for each of the two Ags studied. The flow cytometry analysis has allowed the inventors to observe that the two constructs bind in a preferred and increased manner to the APCs. These observations therefore indicate that the association of a ligand of a specific receptor and a ligand of a ubiquitous molecule, such as HSs, makes it possible to increase the Ag-specific immune response. It was not obvious that combining the targeting of HSs and of specific surface proteins of APCs can increase, and even less so that it can produce a synergy of effect on, the antigen-specific immune response (the antigen presentation is increased by a factor of 700 in the case of alpha toxin). This synergy of effect was all the less obvious because of the ubiquitous expression of HSs. Indeed, the double-targeted compounds could have been distributed on APCs and also on other cells incapable of presenting the Ag, which could have resulted in a decrease in the response compared with compounds targeted only on APC proteins. This multiple targeting system makes it possible to increase the immunogenicity obtained by single targeting.

Consequently, the subject of the present invention is a molecular complex, characterized in that it comprises at least one antigen associated with at least two ligands of surface molecules of antigen-presenting cells, said complex comprising at least one first ligand of a sulfated sugar of the glycosaminoglycan family and one second ligand of a specific surface molecule of antigen-presenting cells, said first ligand being covalently bonded to said antigen and/or to said second ligand.

Definitions

The term "antigen" is intended to mean any substance that can be specifically recognized by the immune system and in particular by the antibodies and the cells of the immune system (B lymphocytes, CD4+ T lymphocytes, CD8+ T lymphocytes).

The expression "antigen-specific immune response" is intended to mean the production of antibodies, and/or the induction of a T-helper response (activation of CD4+ T lymphocytes) and/or cytotoxic T response (activation of CD8+ T lymphocytes) specific for said antigen. This response can in particular be measured, in vitro, by means of a test for stimulation of antigen-specific CD4+ T or CD8+ T lymphocytes. In this test, the specific T lymphocytes are incubated in the presence of live autologous antigen-presenting cells and of antigen.

The term "immunogenicity" of an antigen is intended to mean its ability to induce a specific immune response.

The term "antigen-presenting cell", or "APC", is intended to mean a cell expressing one or more major histocompatibility complex (MHC) class I and class II molecules (HLA class I and class II molecules in humans) and capable of presenting the antigens to the CD4+ T and CD8+ T lymphocytes specific for this antigen. As antigen-presenting cells, mention may in particular be made of dendritic cells (DCs), peripheral blood mononuclear cells (PBMCs), monocytes, macrophages, B lymphocytes, lymphoblastoid lines, and genetically modified human or animal cell lines expressing MHC class I and class II molecules, in particular HLA I and HLA II molecules.

The expression "surface molecule of antigen-presenting cells" is intended to mean a molecule expressed at the surface of antigen-presenting cells.

The expression "specific surface molecule of antigen-presenting cells" is intended to mean a molecule which has a high specificity of expression for APCs, namely a surface molecule expressed on a very limited number of cells other than APCs, i.e. a surface molecule expressed essentially on antigen-presenting cells.

The term "antigen processing" is intended to mean the transformations undergone by the Ag and which allow it to change from a form incapable of binding to MHC molecules to a form capable of binding. These steps of preparing the antigen by live APCs therefore result in the formation of peptide/MHC I molecule or peptide/MHC II molecule complexes. The complexes are subsequently expressed at the surface of the APCs. In order to be processed, generally, the Ag must first of all be endocytosed or phagocytosed by APCs. The processing then takes place mainly in the endocytotic vesicles and in the cytoplasm of the APCs. In these compartments, the Ag undergoes proteolytic degradation and/or denaturation associated with the pH or with oxydoreductases, followed by loading of the peptides onto MHC class I and class II molecules and transport of the peptide/MHC complexes to the surfaces of the APCs.

The term "endocytotic receptor" is intended to mean a receptor capable of mediating the endocytosis of a ligand of this receptor.

The term "glycosaminoglycan" (GAG) is intended to mean a linear polysaccharide composed of the repetition of a disaccharide always containing a hexosamine (glucosamine (GlcN) or galactosamine (GalN)) and another monosaccharide (glucuronic acid (GlcA), iduronic acid (IdoA), galactose (Gal)). Glucosamine is either N-sulfated (GlcNS) or N-acetylated (GlcNac). Galactosamine is always N-acetylated (GalNac). Sulfated glycosaminoglycans are in particular simple polymers of GlcA, such as chondroitin sulfate, and copolymers comprising at the same time GlcA and/or IdoA and/or Gal residues, such as heparin, heparan sulfate, dermatan sulfate and keratan sulfate. The GAG chains may be covalently bonded to proteins (proteoglycans) which are expressed at the surface of mammalian cells and/or secreted into the extracellular medium.

The term ("antibody") is intended to mean an immunoglobulin (IgG, IgM, IgA, IgD, IgE). The term "antibody" includes a specific antibody, i.e. an antibody directed against a particular molecule x (anti-molecule x antibody), and a nonspecific antibody. A specific antibody is in particular an antibody directed against an antigen (anti-antigen antibody) or an APC surface molecule (anti-APC surface molecule antibody).

The term "epitope" is intended to mean the sequence of an antigen which is recognized by an antibody (B epitope), a CD4+ T lymphocyte (CD4+ T epitope) or a CD8+ T lymphocyte (CD8+ T epitope), specific for this antigen. It is in particular a peptide (epitope peptide).

The molecular complex according to the invention comprises at least: one antigen associated with at least two ligands of surface molecules of APCs. In this complex, the first ligand which targets a sulfated GAG is covalently bonded to the antigen and/or to the second ligand.

The covalent bonding is in particular generated by covalent chemical coupling (formation of a covalent conjugate) or by the construction of a fusion protein (genetic fusion).

In accordance with the invention, the ligands are heterologous ligands, i.e. the antigen and the ligands are derived from three different initial molecules, or, when the antigen and one of the ligands or both ligands are derived from the same initial molecule, the fusion protein according to the invention has a sequence which is different than that of the initial molecule. The fusion protein according to the invention comprises at least one mutation (insertion, deletion, substitution) compared with the sequence of the initial molecule.

The molecular complex according to the invention may be an entirely covalent complex in which the first ligand, the second ligand and the antigen are bonded, either solely via covalent chemical couplings or genetic fusions, or via a mixture of the two, one of the bonds being generated by genetic fusion and the other by covalent chemical coupling. For example, the first and the second ligands are covalently bonded (L1-L2) and the antigen is covalently bonded either to L1 or to L2. It is in particular a covalent conjugate Ag-L1-L2 or L1-L2-Ag or a fusion protein Ag-L1-L2, L2-L1-Ag, L1-L2-Ag or Ag-L2-L1. Alternatively, the first ligand is covalently bonded to the antigen and the second ligand is covalently bonded either to L1 or to the Ag. It is in particular a covalent conjugate L1-Ag-L2 or L2-L1-Ag or a fusion protein L1-Ag-L2, L2-Ag-L1, L2-L1-Ag or Ag-L1-L2.

The molecular complex according to the invention may also be a mixed complex in which the bonding of the antigen to L1-L2 (covalent conjugate L1-L2 or fusion protein L1-L2 or L2-L1) or the bonding of the second ligand to L1-Ag (covalent conjugate L1-Ag or fusion protein L1-Ag or Ag-L1) is noncovalent. The noncovalent bonding is obtained by any means known to those skilled in the art. It may in particular be obtained using a molecule (binding element), in particular a peptide, which has a high and specific affinity for L1, L2 or the Ag. This binding element is covalently bonded to the antigen (Ag), to the second ligand (L2), to L1-L2 or L1-Ag, so as to noncovalently associate the antigen with L1-L2 or the second ligand with L1-Ag. The affinity of the binding element for its partner, in the L1-L2/Ag-binding element or L1-Ag/L2-binding element complex, is sufficient for it not to immediately dissociate from this complex in vivo. When one of the ligands is an antibody, the binding element is in particular a protein or a protein fragment which binds the Fc and/or Fab region of immunoglobulins, as described in application FR 2 759 296. Such immunoglobulin-binding elements include in particular *S. aureus* protein A, the BB fragment thereof (SEQ ID NO: 4) and the ZZ derivative thereof (SEQ ID NO: 3), the first two proteins binding the immunoglobulin Fc and Fab regions, whereas ZZ binds only the Fc region. For example, when L2 is an antibody, the immunoglobulin-binding element is covalently bonded (covalent chemical coupling or fusion protein) either to the antigen, or to L1 covalently bonded to the antigen (L1-Ag).

The antigen is optionally covalently or noncovalently associated with other ligands of surface molecules of APCs, in particular with ligands which target the same molecules as the first or the second ligand or else one or more molecules different than the above molecules.

The molecular complex according to the invention binds at least to a sulfated GAG and to a surface molecule expressed essentially on APCs, and then the complex is internalized by the APCs and the antigen is processed by the APCs so as to be presented by the MHC molecules (class I and/or class II) at the surface of the APCs. The antigen associated separately with each of the ligands binds to its surface receptor expressed on the APCs (simple targeting of APCs). Preferably, at least one of the antigen/first ligand and antigen/second ligand complexes, separately formed, preferably the antigen/second ligand complex, is internalized by the APCs and the antigen is processed by the APCs so as to be presented by the MHC molecules (class I and/or class II) at the surface of the APCs. Even more preferably, each of the complexes thus separately formed (antigen/first ligand and antigen/second ligand) is internalized by the APCs and the antigen is processed by the APCs so as to be presented by the MHC molecules (class I and/or class II) at the surface of the APCs.

The processing of the antigen (free or complex with one of the two ligands or with both) by the APCs and the presentation thereof by the MHC molecules (class I and/or class II) at the surface of the APCs can be measured, in vitro, by means of a test for stimulation of CD4+ T or CD8+ T lymphocytes specific for the antigen in the presence of live autologous antigen-presenting cells brought into contact beforehand with said antigen (free or complex with one of the two ligands or with both). The T-stimulating capacity of the free antigen or the antigen complexed with one of the two ligands or with both can thus be measured and compared. The T-stimulating capacity of the antigen is significantly increased with the complex according to the invention, compared with the free antigen or the antigen associated with just one of the ligands.

The antigen is preferably a vaccine antigen such as an antigen specific for a pathogenic agent (virus (HIV, influenza, etc.), bacterium, parasite, fungus, etc.) or for a tumor. It is a natural, recombinant or synthetic antigen, in particular an attenuated or inactivated pathogenic agent (virus, bacterium), synthetic viral particles, an isolated molecule (protein, polysaccharide, lipid, lipoprotein, glycoprotein or lipopolysaccharide) or fragments of molecules comprising one or more B, CD4+ T or CD8+ T epitopes, in particular in the form of peptides or of polypeptides comprising epitopes derived from a single antigen or from several different antigens (polyepitopic fragment).

The sulfated sugar of the glycosaminoglycan family, expressed at the surface of the APCs (sulfated GAG), which is targeted by the first ligand, is preferably a heparan sulfate, a chondroitin sulfate, a dermatan sulfate or a keratan sulfate.

The first ligand is derived from a mammalian cell or from a pathogenic microorganism, in particular a virus (adenovirus, cytomegalovirus, HIV, Sindbis virus), a bacterium (*Mycobacterium bovis, Bordetella pertussis*), a parasite (*Leishmania* sp.) or a toxin; it is in particular a molecular complex, a molecule or one of its fragments which binds heparin, heparan sulfates and/or chondroitin sulfates and which preferably uses sulfated GAG proteoglycans as endocytotic receptor. Such ligands are in particular described in "*Heparan Binding Proteins*", H. Edward Conrad, Academic Press, San Diego and London and Dreyfuss et al., Annuals of the Brazilian Academy of Sciences, 2009, 81, 409-429 (see in particular table II). Examples of these ligands include, in a nonlimiting manner: the HIV Tat protein and fragments thereof, in particular the fragments comprising only the basic region of Tat (Tat 49-57: RKKRRQRRR: SEQ ID NO: 1) or the basic region and the central region of Tat (this central or core region consists of Tat 38-48: FTKKGLGI-SYG: SEQ ID NO: 5); dodecahedra derived from the adenovirus penton (Vives et al., Virology, 2004, 321: 332-340); the envelope protein of HIV or the V3 region of this protein (Roderiquez et al., J. Virol., 1995, 69, 2233-), the envelope glycoprotein of the Sindbis virus (Byrnes, A. P. and Griffin, D. E., J. Virol., 1998, 2, 7349-7356) and the R domain of the diphtheria toxin (fragment 382 to 535 (SEQ ID NO: 6): Lobeck et al., Infection and Immunity, 1998, 66, 418-423). Mention may also be made of the cell penetrating peptides (CPPs) which bind heparin, heparan sulfates and/or chondroitin sulfates, such as the peptides very rich in basic residues, in particular in arginines, which include the peptides derived from the basic region of the HIV Tat protein (Tat 49-57), mentioned above, and the polyarginine peptides (R7 to R11), and also the basic/amphiphilic peptides such as the peptides derived from the homeodomain of the antennapedia protein (penetratin; fragment 43-58: RQIKIWFQN-RRMKWKK (SEQ ID NO: 2)).

Alternatively, the first ligand is a natural or recombinant antibody directed against a sulfated GAG, preferably heparin, heparan sulfates or chondroitin sulfates, or a fragment of this antibody containing at least the paratope (antigen-binding domain), such as a Fab, Fab', F(ab')$_2$, Fv or single-chain Fv (scFv) fragment, Fabc fragment and Fab fragment comprising a portion of the Fc domain. Such antibodies are in particular described in Thompson et al., J. Biol. Chem., 2009, 284, 35621-35631 and van Kuppevelt et al., J. Biol., Chem., 1998, 273, 12960-12966. Preferably, said antibody or antibody fragment is human or humanized.

According to one advantageous embodiment of the molecule complex according to the invention, the ligand of the sulfated glycosaminoglycan expressed at the surface of APCs is a peptide selected from the group consisting of: a fragment of the HIV Tat protein, comprising at least the basic region (Tat 49-57), such as the Tat 49-57 (SEQ ID NO: 1) and Tat 37-57 (CFTKKGLGISYGRKKRRQRRR: SEQ ID NO: 7) peptides, a polyarginine peptide R7 to R11, and a peptide comprising the R domain of the diphtheria toxin (fragment 382 to 535: SEQ ID NO: 6).

The molecule expressed at the surface of APCs, which is targeted by the second ligand and optionally the other ligands (third, etc.), is a surface molecule expressed essentially on APCs and in particular on dendritic cells. Preferably, said surface molecule of APCs is an endocytotic receptor. Among these surface molecules, mention may in particular be made of: MHC molecules (class I and II), surface immunoglobulins, integrins (CD11c, MAC1), transferrin receptors, C-type lectin receptors (mannose receptor (CD206), DEC-205 (CD205), DC-SIGN (CD209), LOX1, Dectin-1 (beta-glucan receptor), Dectin-2, Clec9A, Clec12A, DCIR2, FIRE, CIRE), receptors for the immunoglobulin constant region (FcR and in particular FcγR: FcγR1 (CD64), FcγRII (CD32), FcγRIII (CD16)), the TNF receptor (CD40) superfamily, and complement receptors.

According to another advantageous embodiment of the molecular complex according to the invention, the molecule expressed at the surface of APCs which is targeted by the second ligand and optionally the other ligands is selected from the group consisting of: MHC class II molecules, C-type lectin receptors, immunoglobulins and receptors for the immunoglobulin constant region (FcR).

The second ligand and optionally the other ligands are in particular natural ligands of these surface molecules of APCs, in particular saccharides which bind C-type lectin receptors, immunoglobulins and fragments thereof comprising the constant region which bind FcRs, proteins or protein fragments which bind the immunoglobulin Fc and/or Fab region, as described in application FR 2 759 296 (surface immunoglobulin), or envelope proteins of viruses (HIV, dengue virus, sindbis virus, etc.) which use these surface molecules of APCs as endocytotic receptors. Alternatively, the second ligand and optionally the other ligands are natural or recombinant antibodies directed against these surface molecules of APCs or fragments of these antibodies containing at least the paratope (antigen-binding domain), such as the Fab, Fab', F(ab')$_2$, Fv or single-chain Fv (scFv) fragments, Fabc fragment and Fab fragment comprising a portion of the Fc domain. Preferably, said antibody or antibody fragment is human or humanized.

According to one advantageous arrangement of the above embodiments, the complex according to the invention comprises: (i) an antigen covalently bonded to a sulfated-GAG ligand peptide as defined above (first ligand), (ii) an antibody directed against said antigen, preferably an IgG (second ligand), and optionally a protein or a protein fragment which binds the antibody Fab region, such as *Staphylococcus aureus* protein A.

According to another advantageous arrangement of the above embodiments, the complex according to the invention comprises: (i) an antigen, (ii) an antibody specific for said antigen, preferably an IgG, or a fragment of said antibody comprising at least the Fc region (second ligand), covalently bonded to a sulfated-GAG ligand peptide as defined above (first ligand), and optionally a protein or a protein fragment which binds the antibody Fab region, such as *Staphylococcus aureus* protein A. Preferably, the antibody is a whole immunoglobulin and the complex also comprises a protein or a protein fragment which binds the antibody Fab region, such as *Staphylococcus aureus* protein A.

According to another advantageous arrangement of the above embodiments, the complex according to the invention comprises: (i) an antigen covalently bonded to a protein or a protein fragment which binds the antibody Fab and/or Fc region, preferably only the Fab region, such as *S. aureus* protein A or the BB fragment thereof (binding element), (ii) an antibody (nonspecific or specific for said antigen), preferably an IgG, or a fragment of said antibody comprising at least the Fc region (second ligand), covalently bonded to a sulfated-GAG ligand peptide as defined above (first ligand), and optionally a protein or a protein fragment which binds the antibody Fab region, such as *Staphylococcus aureus* protein A, when the antigen is not already bound thereto. Preferably, the antibody is a whole immunoglobulin and the antigen is covalently bonded to a protein or a protein fragment which binds only the antibody Fab region, such as *S. aureus* protein A and the BB fragment thereof.

According to another advantageous arrangement of the above embodiments, the complex according to the invention comprises: (i) an antigen covalently bonded to a sulfated-GAG ligand peptide as defined above (first ligand), and to a protein or a protein fragment which binds the antibody Fc and/or Fab region, preferably only the Fab region, such as *Staphylococcus aureus* protein A and the BB fragment thereof (binding element), (ii) an antibody (nonspecific or specific for said antigen), preferably an IgG, or a fragment of said antibody comprising at least the Fc region (second ligand), and optionally a protein or a protein fragment which binds the antibody Fab region, such as *S. aureus* protein A, when the antigen is not already bound thereto. Preferably, the antibody is a whole immunoglobulin and the antigen is covalently bonded to a protein or a protein fragment which binds only the antibody Fab region, such as *S. aureus* protein A and the BB fragment thereof.

According to another advantageous arrangement of the above embodiments, the complex according to the invention comprises an antigen covalently bonded to a sulfated-GAG ligand peptide as defined above (first ligand) and to a protein or a protein fragment which binds the immunoglobulin Fc and/or Fab region, such as the BB fragment of *Staphylococcus aureus* protein A and the ZZ derivative thereof (second ligand).

According to another advantageous arrangement of the above embodiments, the complex according to the invention comprises an antigen covalently bonded to a sulfated-GAG ligand peptide as defined above (first ligand) and to an antibody selected from the group consisting of an anti-MHC class II antibody, an anti-FcgammaR (I, II and/or III) antibody and an anti-DEC-205 antibody, or else to a fragment of the above antibodies, comprising at least the paratope, such as, for example, a Fab, Fab', F(ab')$_2$, Fv or scFv fragment, Fabc fragment or Fab fragment comprising a portion of the Fc region (second ligand).

According to yet another advantageous arrangement of the above embodiments, the complex according to the invention comprises: (i) an antigen covalently bonded to a sulfated-GAG ligand peptide as defined above (first ligand) and to a protein or a protein fragment which binds the immunoglobulin Fc and/or Fab region, such as the BB fragment of *Staphylococcus aureus* protein A and the ZZ derivative thereof (binding element), and (ii) an antibody selected from the group consisting of an anti-MHC class II antibody, an anti-FcgammaR (I, II and/or III) antibody, and an anti-DEC-205 antibody, or a fragment of the above antibodies comprising at least the paratope, in particular a Fab, Fab', F(ab')$_2$, Fv or scFv fragment, Fabc fragment or Fab fragment comprising a portion of the Fc region (second ligand).

According to yet another advantageous arrangement of the above embodiments, the complex according to the invention comprises: (i) an antigen covalently bonded to a protein or a protein fragment which binds the immunoglobulin Fc and/or Fab region, such as the BB fragment of *Staphylococcus aureus* protein A and the ZZ derivative thereof (binding element), and (ii) an antibody selected from the group consisting of an anti-MHC class II antibody, an anti-FCgammaR (I, II and/or III) antibody, and an anti-DEC-205 antibody, or a fragment of the above antibodies comprising at least the paratope, in particular a Fab, Fab', F(ab')$_2$, Fv or scFv fragment or Fab fragment comprising a portion of the Fc region (second ligand), covalently bonded to a sulfated-GAG ligand peptide as defined above (first ligand).

Those skilled in the art are well aware of the species specificities of biomolecules and in particular of proteins. Consequently, those skilled in the art will easily recognize the advantage of targeting the surface molecules of the same species as the species to be immunized and of using ligands of the same species as the species to be immunized or the sequence of which has been adapted to this species. For example, for preparing a human vaccine, it is preferable to use human or humanized antibodies directed against a human surface molecule.

A subject of the present invention is also an isolated polynucleotide, an isolated polynucleotide construct or else a mixture of polynucleotides or of polynucleotide constructs, selected from the group consisting of:

a) an isolated polynucleotide comprising a sequence encoding a fusion protein comprising at least the coding sequences of the antigen, of the first ligand and of the second ligand fused in-frame in a suitable manner, b) a mixture of polynucleotides comprising at least one first polynucleotide comprising a sequence encoding a fusion protein comprising at least the coding sequences of the antigen and of the first ligand, fused in-frame in a suitable manner, and a second polynucleotide comprising a sequence encoding the second ligand, said first or second nucleotide also comprising a sequence encoding a binding element as defined above, c) a mixture of polynucleotides comprising a first polynucleotide comprising a sequence encoding a fusion protein comprising at least the coding sequences of the first ligand and of the second ligand, fused in-frame in a suitable manner, and a second polynucleotide comprising a sequence encoding the antigen, said first or second nucleotide also comprising a sequence encoding a binding element as defined above, d) an isolated polynucleotide construct or a mixture of polynucleotide constructs comprising at least the polynucleotide as defined in a) or the two polynucleotides as defined in b) or c), functionally linked to suitable regulatory sequences for transcription and/or for translation (promoter, transcription enhancer, transcription terminator, polyadenylation signal) for the expression of the first ligand, of the antigen and/or of the second ligand in host cells.

The polynucleotides according to the invention encode antigens or ligands which are proteins, peptides or, optionally, glyco- or lipopeptides or glyco- or lipoproteins.

A subject of the present invention is also an isolated recombinant vector or a mixture of recombinant vectors comprising the sequences encoding the antigen, the first ligand and the second ligand, inserted into an isolated polynucleotide or polynucleotide construct, or a mixture of polynucleotides or of polynucleotide constructs, as defined above.

The mixture of recombinant vectors comprises at least one first vector comprising the first polynucleotide or the derived polynucleotide construct as defined in b), c) and d) and a second vector comprising the second polynucleotide or the derived polynucleotide construct as defined in b), c) and d).

Numerous vectors into which it is possible to insert a polynucleotide of interest in order to introduce it into and maintain it in a eukaryotic host cell are known per se; the choice of an appropriate vector depends on the use envisioned for this vector (for example, replication of the sequence of interest, expression of this sequence, maintaining of the sequence in extrachromosomal form or else integration into the chromosomal material of the host), and also on the nature of the host cell. It is possible to use, inter alia, viral vectors (adenovirus, retrovirus, lentivirus, AAV) and nonviral vectors (naked DNA), in particular a plasmid, into which the sequence of interest has been inserted beforehand.

Preferably, said recombinant vector(s) is (are) expression vectors comprising at least one polynucleotide construct as defined above. The expression vectors can be used for the production of the complex according to the invention in suitable host cells or as a vaccine.

Preferably, the recombinant vector according to the invention is an expression plasmid, which can be used both for the production of the complex according to the invention and as a naked DNA vaccine.

A subject of the present invention is also prokaryotic or eukaryotic cells transformed with a recombinant vector as defined above.

A subject of the present invention is also an immunogenic or vaccine composition comprising at least one molecular complex as defined above, a polynucleotide or a mixture of polynucleotides comprising the coding sequences of the antigen, of the first ligand and of the second ligand, preferably inserted into one or more polynucleotide constructs or expression plasmids, as defined above, and a pharmaceutically acceptable vehicle.

The vaccine composition comprises an amount of complex(es), polynucleotide(s) and/or vector(s) which is sufficient to induce an immune response specific for a pathogen or for a tumor, capable of protecting against infection with this pathogen or of reducing the consequences thereof or else of reducing the growth of a tumor, in an individual vaccinated with this composition.

The pharmaceutically acceptable vehicles are those conventionally used.

The vaccine composition optionally also comprises a humoral and/or cellular immunity adjuvant. The adjuvants are advantageously chosen from the group consisting of: oily emulsions, mineral substances, bacterial extracts, saponin, alumina hydroxide, monophosphoryl lipid A, squalene and TLR ligands, in particular oligonucleotides comprising at least one CpG sequence which are ligands of TLR9.

The vaccine composition according to the invention is in a galenical form suitable for parenteral (subcutaneous, intramuscular, intravenous), enteral (oral, sublingual) or local (rectal, vaginal) administration.

The isolated polynucleotides or the polynucleotides inserted into a plasmid vector are introduced into the individual to be vaccinated, either using physical methods such as electroporation, or by associating them with any substance(s) making it possible to cross the plasma membrane, such as transporters, for instance nanotransporters, liposomes, lipids or cationic polymers. In addition, these methods can advantageously be combined, for example by using electroporation combined with liposomes.

Preferably, said composition also comprises a carrier substance. The carrier substances are those conventionally used. They may in particular be unilamellar or multilamellar liposomes, ISCOMS, virosomes (virus-like particles), saponin micelles, solid microspheres which are saccharide in nature (poly)lactide-co-glycolide)) or gold in nature, and nanoparticles.

The vaccine composition may comprise several molecular complexes comprising different antigens and/or ligands or else at least one other antigen of interest (not complexed with ligands according to the invention) or a polynucleotide or plasmid vector encoding said antigen, as defined above. Said complex(es) is (are) optionally bonded together via covalent or noncovalent bonds and/or incorporated inside or at the surface of a particle such as a liposome or a virosome.

A subject of the present invention is also a molecular complex, an isolated polynucleotide or a polynucleotide inserted into a polynucleotide construct or an expression plasmid, according to the invention, as a vaccine for preventing or treating an infectious disease or a cancer.

The antigen targeting complexes according to the invention are prepared by the conventional techniques known to those skilled in the art, namely:

the antigen, and the ligands of the surface molecules of APCs, can be produced by chemical synthesis or by expression of a recombinant DNA in a suitable eukaryotic or prokaryotic cell system. The peptides and proteins can be synthesized in the solid phase, according to the Fmoc technique, originally described by Merrifield et al. (J. Am. Chem. Soc., 1964, 85, 2149-), and purified by reverse-phase high performance liquid chromatography. The polypeptides and the proteins can be produced from the corresponding cDNAs, cloned into a suitable eukaryotic or prokaryotic expression vector; the polypeptides or proteins produced in the cells modified with the recombinant vector are purified by any suitable means, in particular by affinity chromatography. Antibodies directed against surface molecules of APCs are well known and commercially available. By way of nonlimiting example, the anti-CD205 (#555831), anti-CD206 (#555952), anti-CD209 (#551186) and anti-HLA-DR (#555556) antibodies are available from Becton-Dickinson. Alternatively, monoclonal antibodies can be produced by the conventional techniques known to those skilled in the art. For example, the monoclonal antibodies are produced from hybridomas obtained by fusion of B lymphocytes of an animal immunized with the surface molecule of APCs, with myelomas, according to the technique of Köhler and Milstein (Nature, 1975, 256, 495-497); the hybridomas are cultured in vitro, in particular in fermenters, or produced in vivo, in the form of ascites; alternatively, said monoclonal antibodies are produced by genetic engineering as described in U.S. Pat. No. 4,816,567. The humanized antibodies are produced by general methods such as those described in International Application WO 98/45332. Antibody fragments are produced from the cloned $V_H$ and $V_L$ regions, or from mRNAs of hybridomas or of splenic lymphocytes of an immunized mammal; for example, the Fv, scFv or Fab fragments are expressed at the surface of filamentous phages according to the technique of Winter and Milstein (Nature, 1991, 349, 293-299); after several selection steps, the antibody fragments specific for the antigen are isolated and expressed in a suitable expression system, by the conventional techniques of recombinant DNA cloning and expression. The antibodies or fragments thereof as defined above are purified by the conventional techniques known to those skilled in the art, such as affinity chromatography;

the covalent association of the first ligand (L1) with the antigen (Ag) and/or with the second ligand (L2) of a surface molecule of APCs can be carried out by constructing a fusion protein in which the nucleotide sequences encoding L1, the Ag and/or L2 are fused in-frame, in the appropriate order, directly, or by means of a nucleotide sequence encoding a suitable linker peptide. Depending on the respective sizes of the amino acid sequences of L1, the Ag and/or L2, they are either fused at their ends (N-terminal end of one of the sequences fused to the C-terminal end on the other sequence) or one of the sequences is inserted into the other sequence at an appropriate site which has no detrimental effect on the immunogenicity of the antigen and the binding of the ligand(s) to its (their) receptor expressed at the surface of the APCs. Alternatively, the antigen and the ligand(s) can be covalently coupled, by any appropriate means. The coupling is carried out by means of reactional groups initially present on or introduced beforehand onto the antigen and the ligand(s). The coupling can in particular be carried out at amino acid residues of which the side chain comprises a reactive function. Among these amino acids, mention may be made of polar amino acids comprising a function: —OH [serine (S), threonine (T) or tyrosine (Y)], —SH [cysteine (C)], —NH$_2$ [lysine (K) or arginine (R)], —COOH (aspartic acid (D) or glumatic acid (E)], and polar amino acids with a side chain functionalized by addition of a reactive function, in particular a chloroacetyl or bromoacetyl which is reactive with thiol groups or a hydrazine group which is reactive with aldehydes. The antigen is coupled to the ligand by any appropriate means; these means, which are known to those skilled in the art, include in particular coupling using homobifunctional reagents, such as glutaraldehyde or dithiobis(succinimidyl propionate). Preferably, the coupling is carried out using heterobifunctional reagents, in particular m-maleimidobenzoyl-N-hydroxysuccinimide (SMCC) or sulfo-SMCC which each contain a maleimide group capable of reacting with free thiols. In this case, the SMCC is covalently bonded beforehand to an amine function present on the Ag or the ligand. At the same time, another heterobifunctional reagent (such as N-succinimidyl S-acetylthioacetate which contains a thioester group that can be cleaved with hydroxylamine, or succinimidyl pyridyl dithiopropionate, which contains a disulfide bridge that can be reduced under mild conditions) is associated with an amine function of the second partner which is either the Ag or one of the ligands. The second partner is then treated with hydroxylamine or with a reducing agent in order to allow release of the thiol. The thiolated compound is then incubated with the compound having incorporated the maleimide and the coupling is obtained by reaction of the thiol group with the maleimide group. This type of covalent coupling is in particular described in Léonetti et al., J. Exp. Med., 1999, 189, 1217-1228. It is also possible to free a thiol group already present on one of the compounds so as to subsequently carry out coupling thereof to another compound which has been modified beforehand using SMCC. This method, which is often used for coupling antibodies to ligands, is in particular described in Ishikawa et al., J. Immunoassay, 1983, 4, 209-327;

the noncovalent complexes are prepared by bringing the second ligand (L2) into contact with the antigen covalently bonded to the first ligand (L1-Ag, the order of L1 and of the Ag being without distinction when it is a question of a fusion protein) or bringing the antigen into contact with the first and the second ligand which are covalently bonded (L1-L2, the order of L1 and L2 being without distinction when it is a question of a fusion protein), under conditions which allow the two partners to interact. This interaction can involve a binding element, in particular a protein or a peptide, which has a high affinity and is specific for one of the partners of the complex (Ag, L1 or L2). In particular, the affinity of the binding element for this partner, in the complex, is sufficient for it not to immediately dissociate from this complex in vivo. When one of the ligands is an immunoglobulin, the binding element is an element for binding to immunoglobulins, as described in application FR 2 759 296. For example, an element for binding to immunoglobulins is covalently bonded to the antigen, so as to form a noncovalent complex with L1-L2. Alternatively, an element for binding to immunoglobulins is covalently bonded to the antigen covalently bonded to L1 (L1-Ag), so as to form a noncovalent complex with L2;

the polynucleotides according to the invention are obtained by the conventional methods, known per se, according to the standard protocols such as those described in Current Protocols in Molecular Biology (Frederick M. AUSUBEL, 2000, Wiley and Sons Inc. Library of Congress, USA). For example, they can be obtained by amplification of a nucleic sequence by PCR or RT-PCR, by screening genomic DNA libraries by hybridization with a homologous probe, or else by total or partial chemical synthesis. The recombinant vectors are constructed and introduced into host cells by conventional recombinant DNA and genetic engineering methods, which are known per se.

The implementation of the invention uses, unless otherwise indicated, conventional immunology, cell culture, cell biology, molecular biology and recombinant DNA methods which are known to those skilled in the art. These techniques are described in detail in the literature, reference should be made for example to: Current Protocols in Molecular Biology (Frederick M. AUSUBEL, 2000, Wiley and Sons Inc, Library of Congress, USA); Current Protocols in Immunology (John E. Coligan et al., 2008, Wiley and Sons Inc, Library of Congress, USA), Molecular Cloning: A Laboratory Manual, Third Edition, (Sambrook et al., 2001, Cold Spring Harbor, N.Y.: Cold Spring Harbor Laboratory Press); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York); specifically, Vols. 154 and 155 (Wu et al. eds.) and Vol. 185, "Gene Expression Technology" (D. Goeddel, ed.); Gene Transfer Vectors for Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986). Antibodies: A Laboratory Manual, E. Howell and D. Lane, Cold Spring Harbor Laboratory, 1988.

Compared with the antigen targeting complexes of the prior art which target a surface molecule specific for antigen-presenting cells (simple targeting), the complex according to the invention allows a double targeting of the antigen onto a ubiquitous surface molecule, a polysulfated sugar of the glycosaminoglycan family, and onto a surface molecule specific for antigen-presenting cells. The double targeting of the antigen onto the antigen-presenting cells with the complex of the invention significantly increases the antigen-specific immune response compared with the simple targeting with the prior art complexes. In addition, for at least some ligands, the double targeting with the complex of the invention produces a synergistic effect on the antigen-specific immune response compared with the simple targeting with the prior art complexes. Because of its increased immunogenicity, the antigen targeting complex according to the invention has the following advantages over the prior art complexes:

it induces a greater protective effect, making it possible to improve vaccine efficacy;

it makes it possible to limit the number of booster administrations to be carried out;

it makes it possible to reduce the doses injected;

it makes it possible to dispense with the use of immunity adjuvants.

Figure 2:
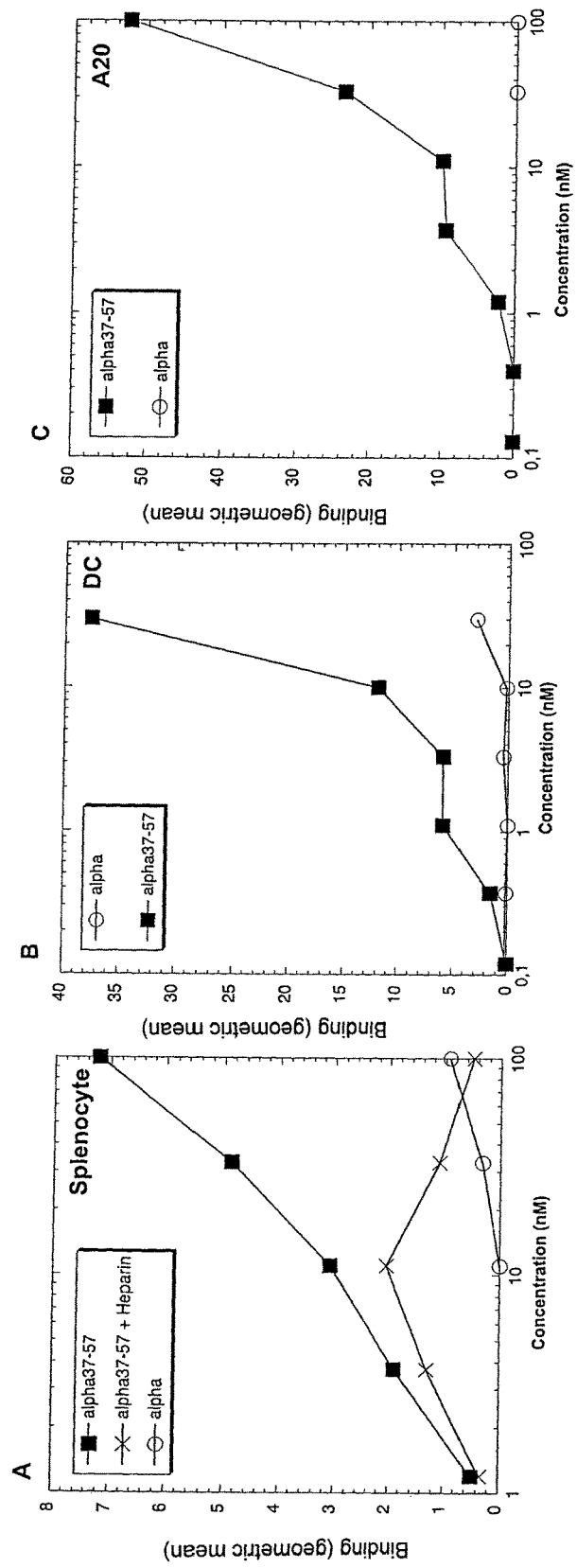
Figure 3:
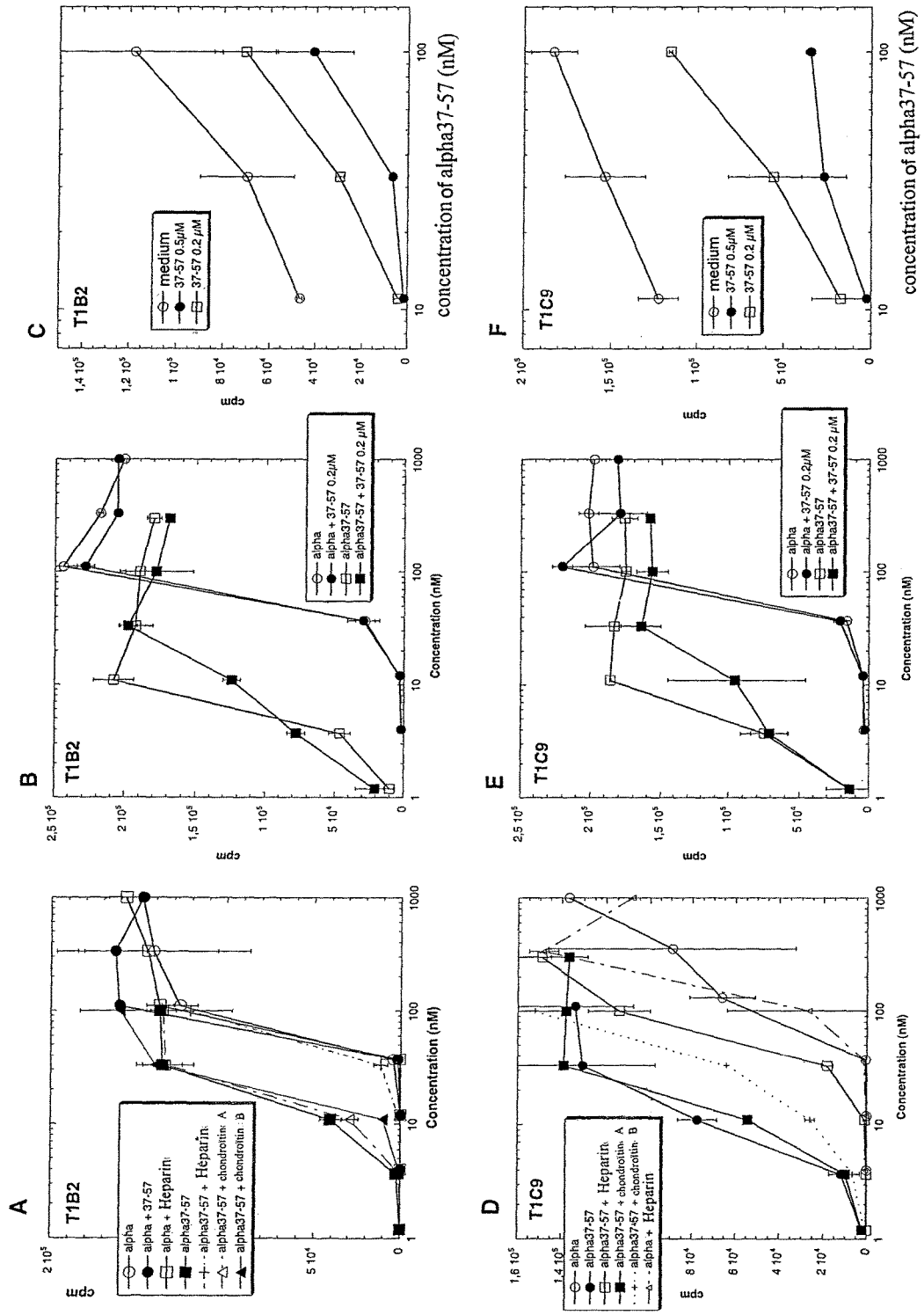
Figure 4:
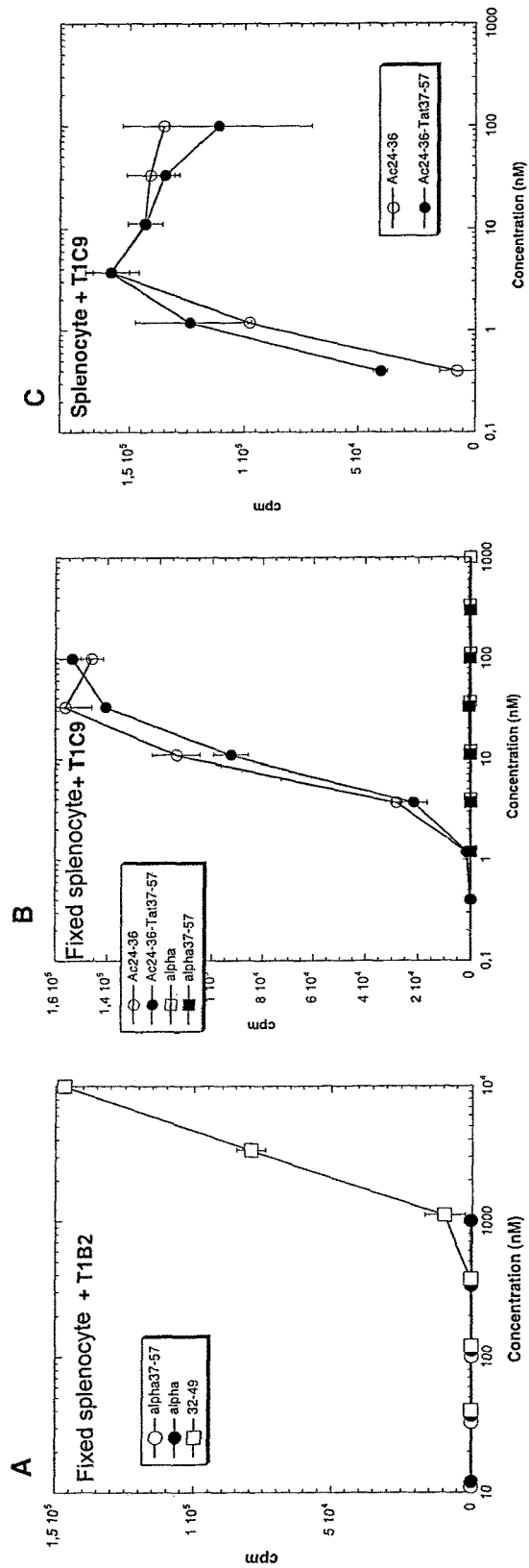
Figure 5:
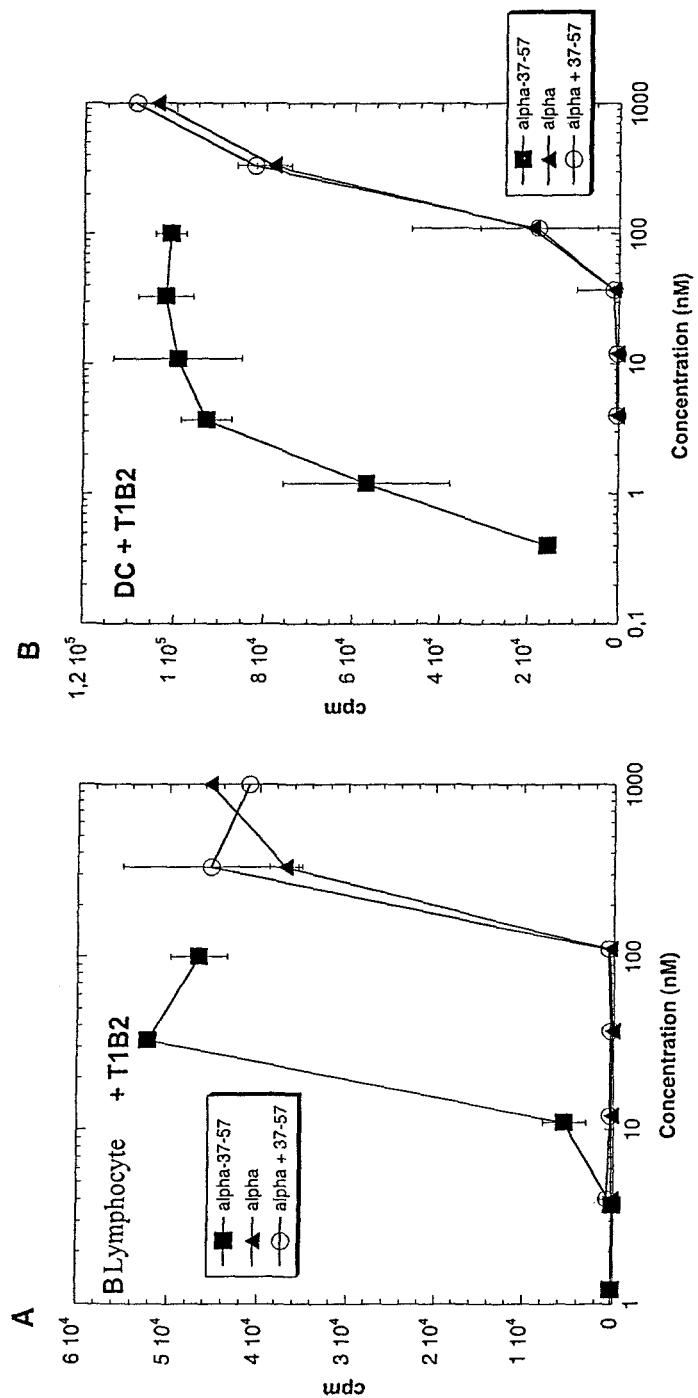
Figure 6:
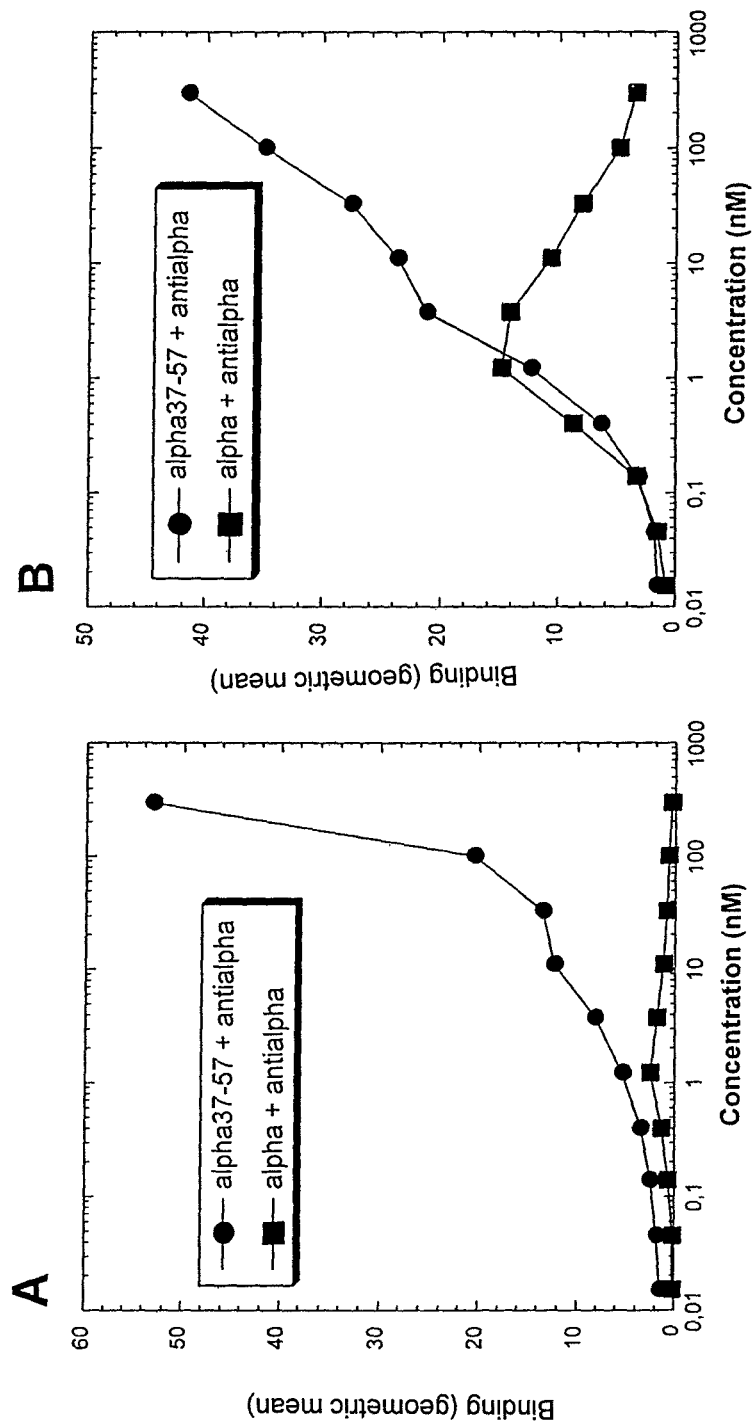
Figure 7:
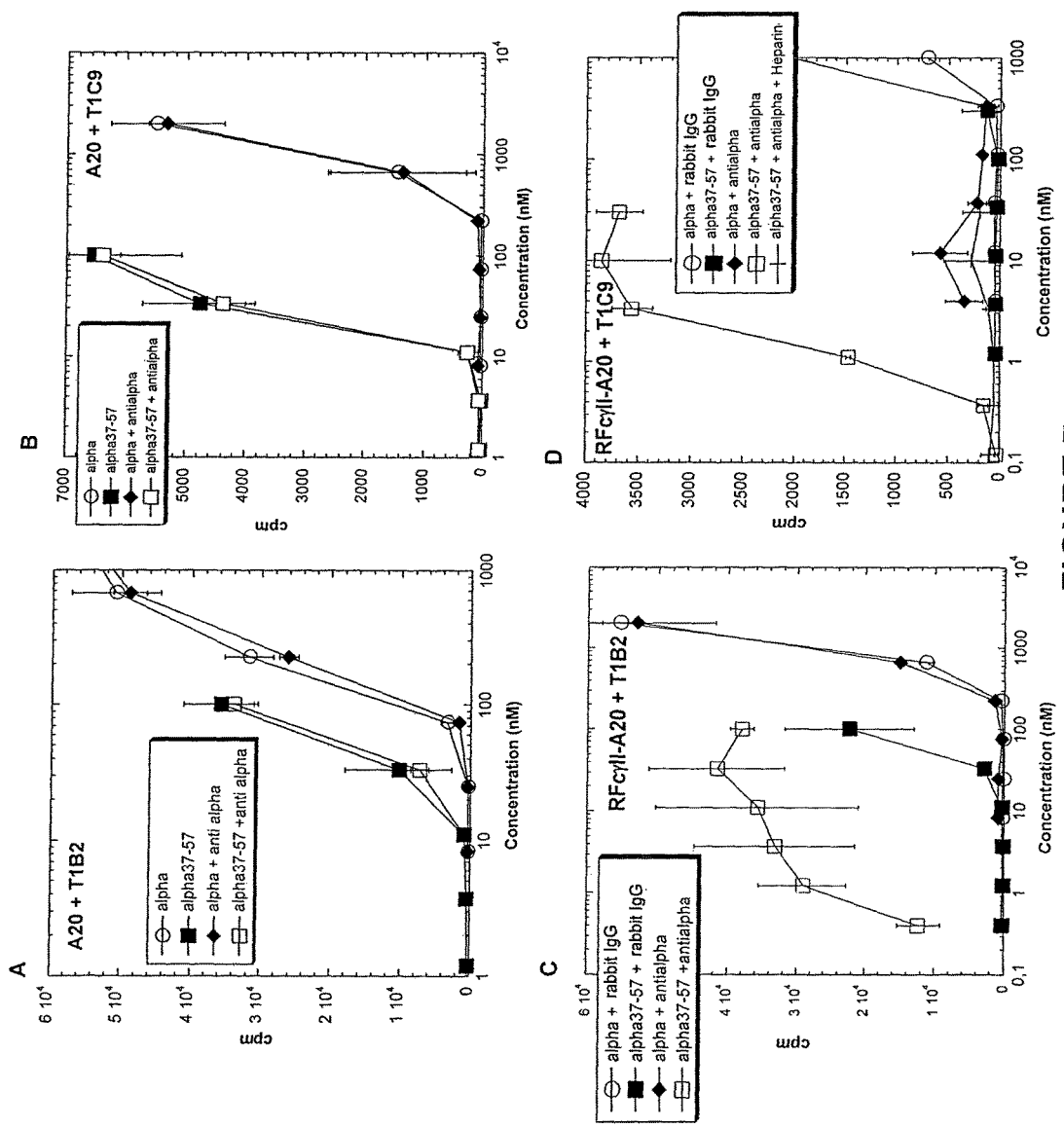
Figure 8:
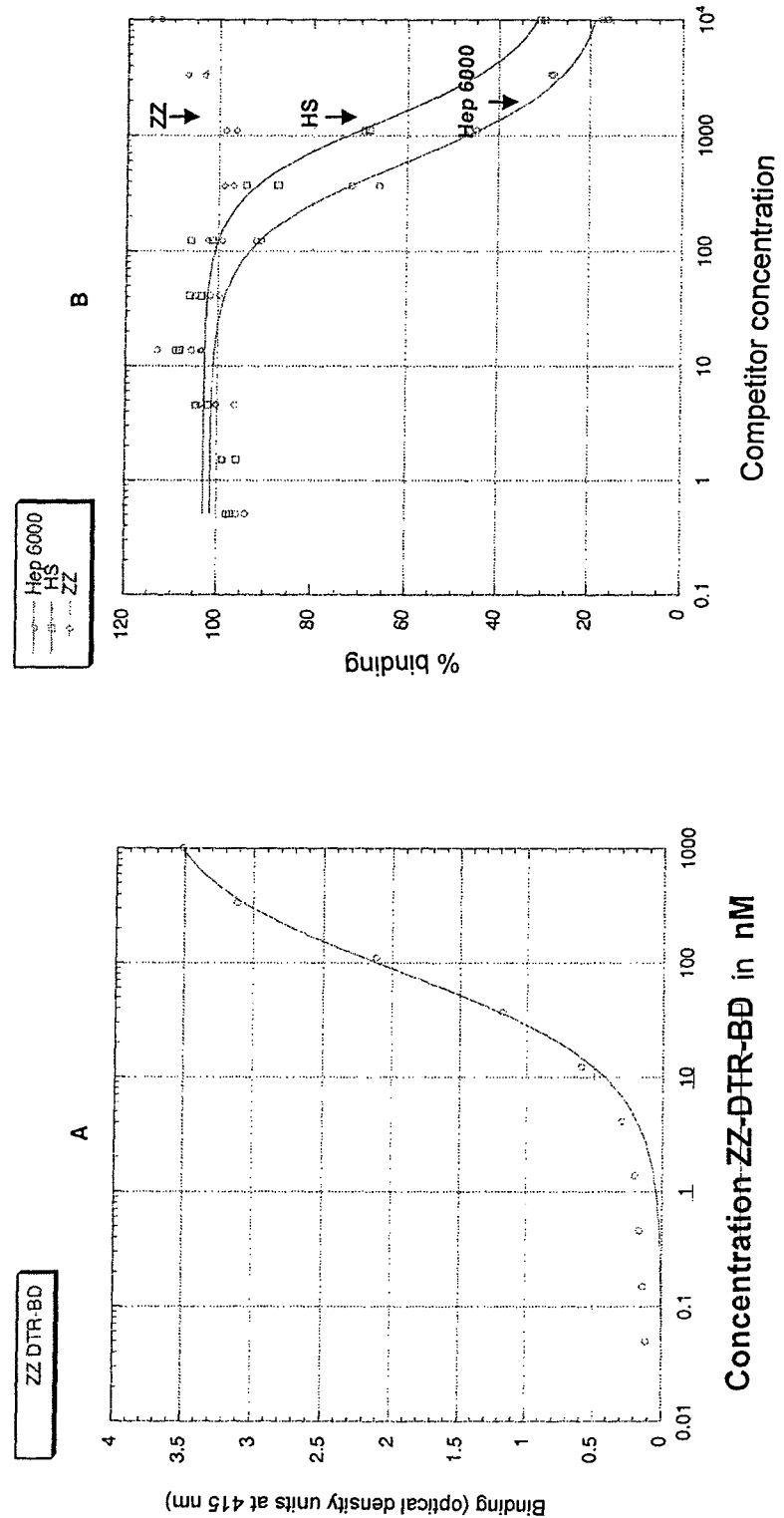
Figure 9:
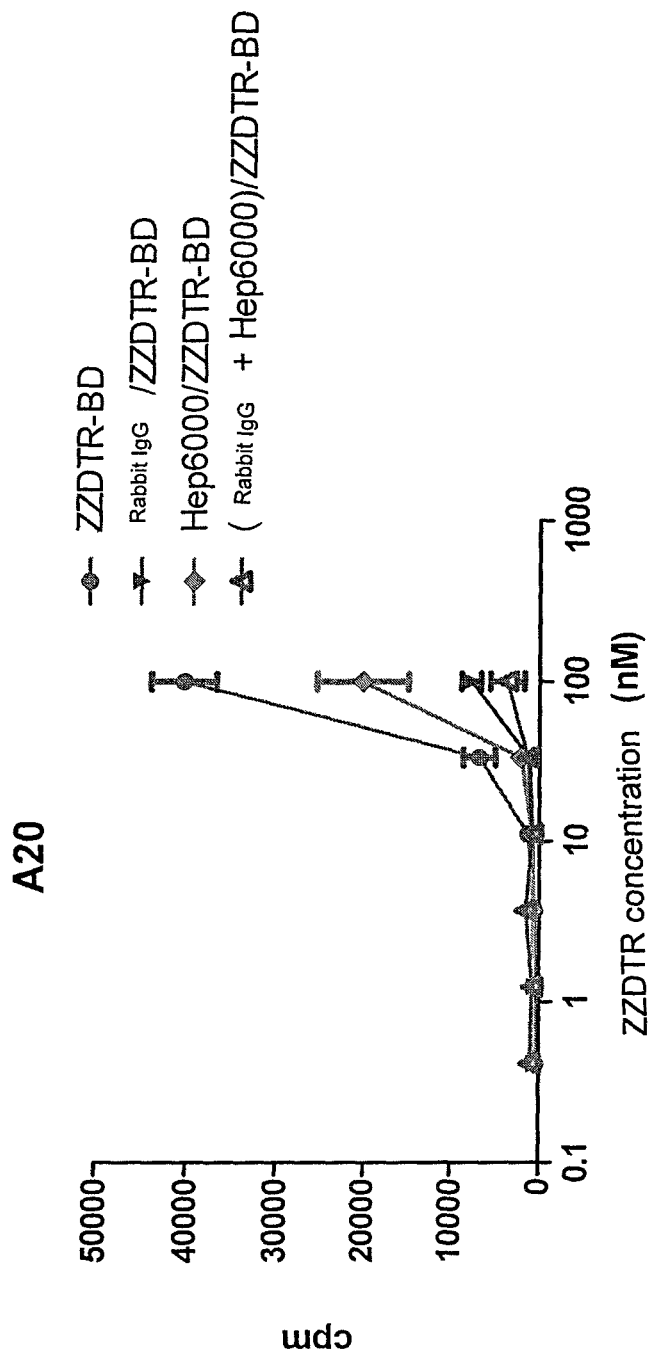
Figure 10:
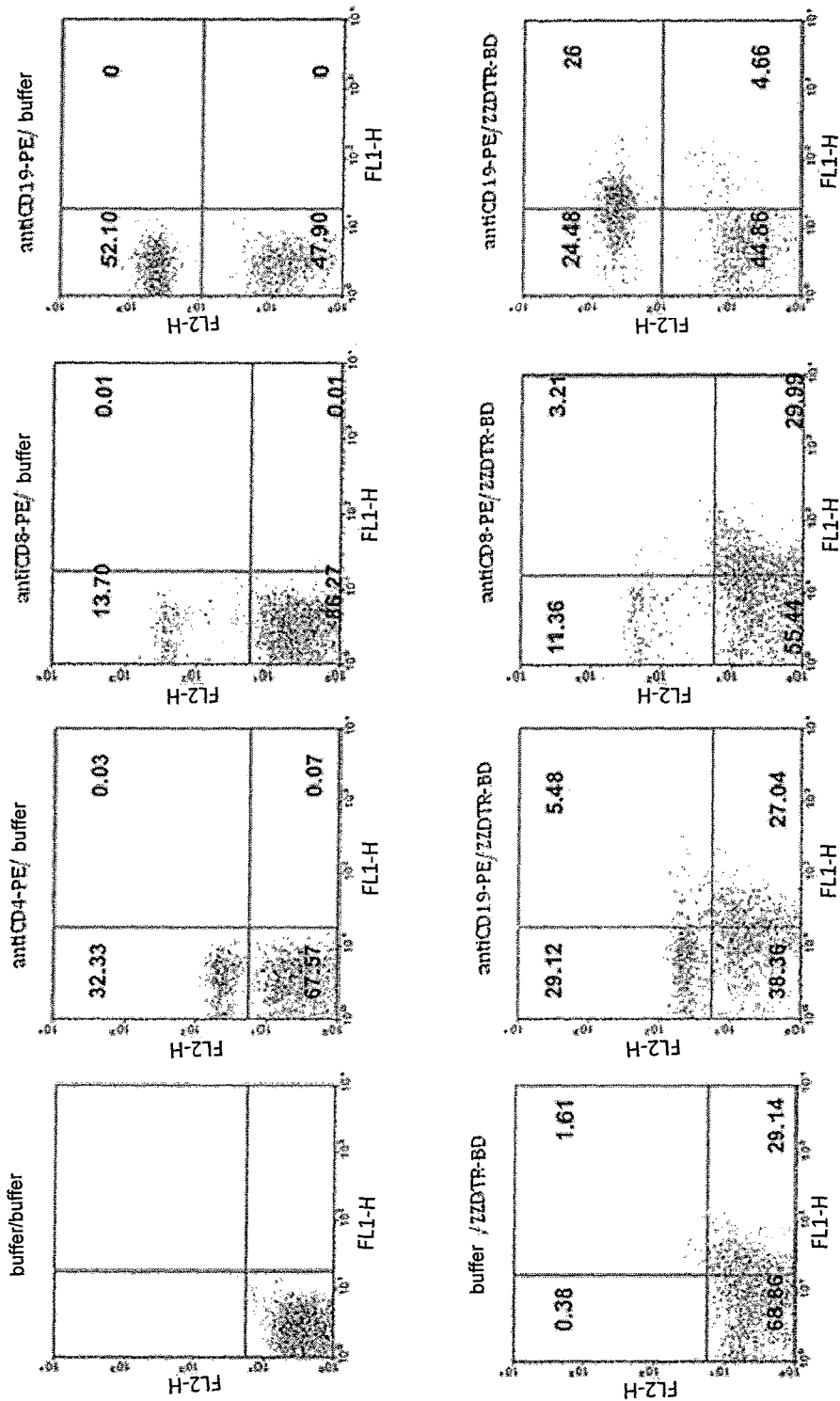
Figure 11:
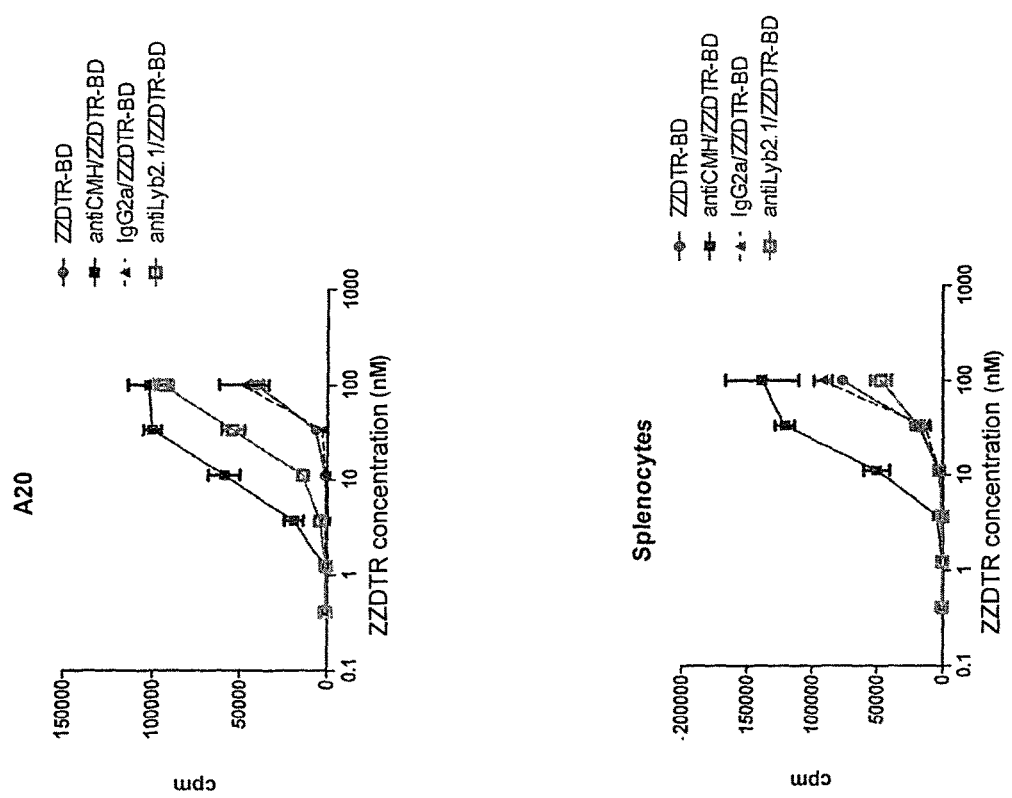
Figure 12:
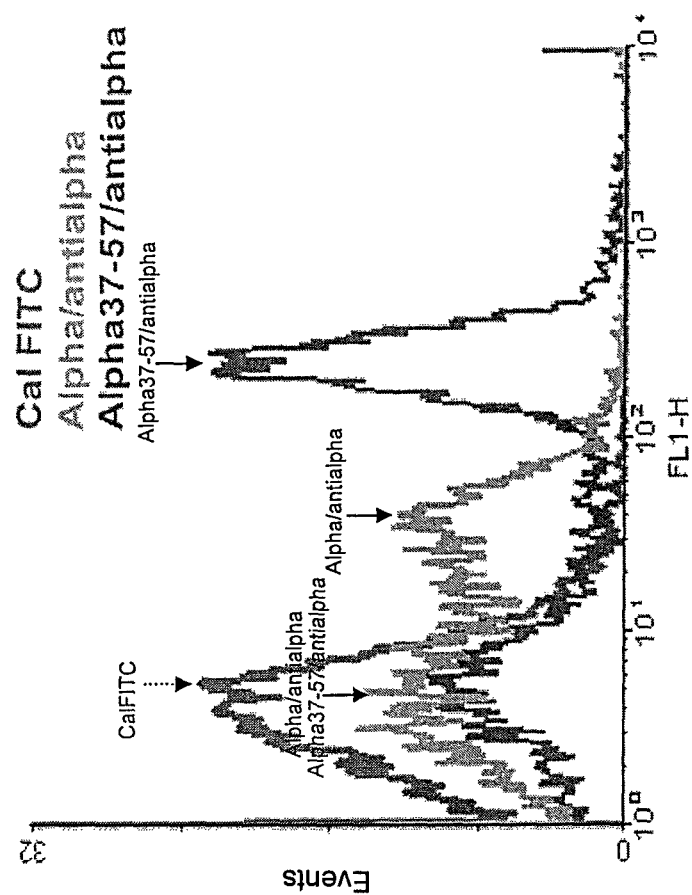
Figure 13:
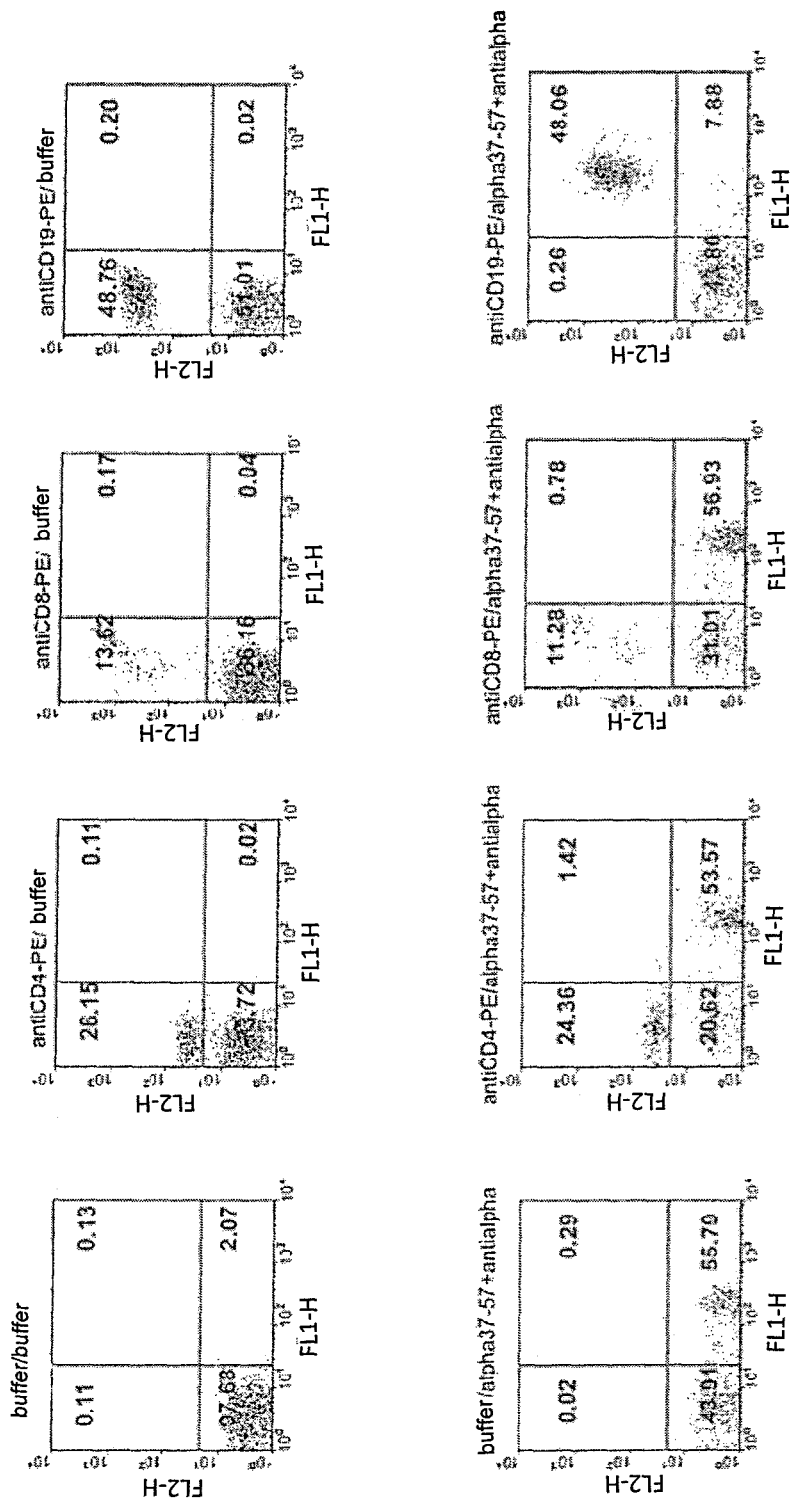
Figure 14:
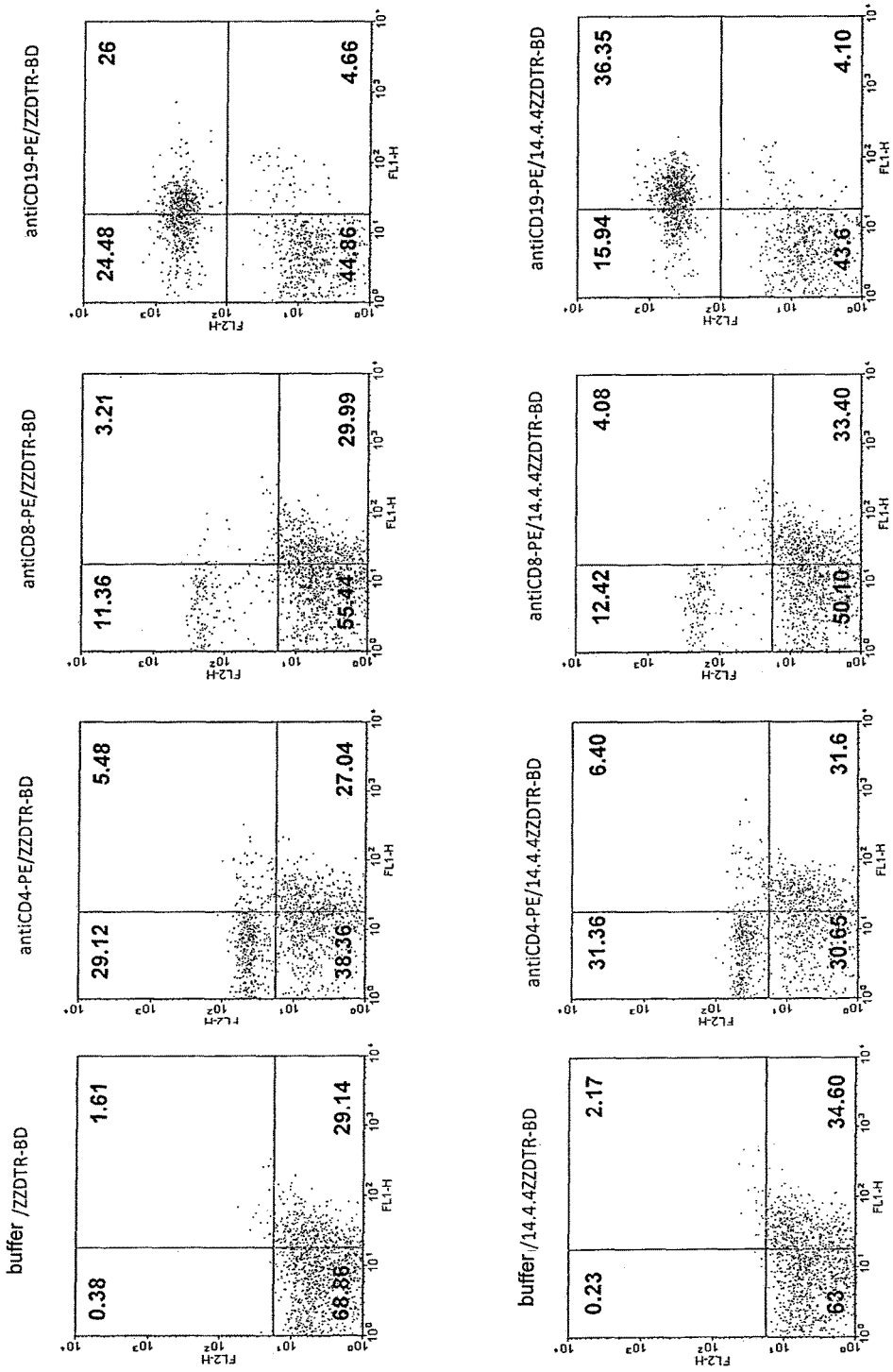
Figure 15:
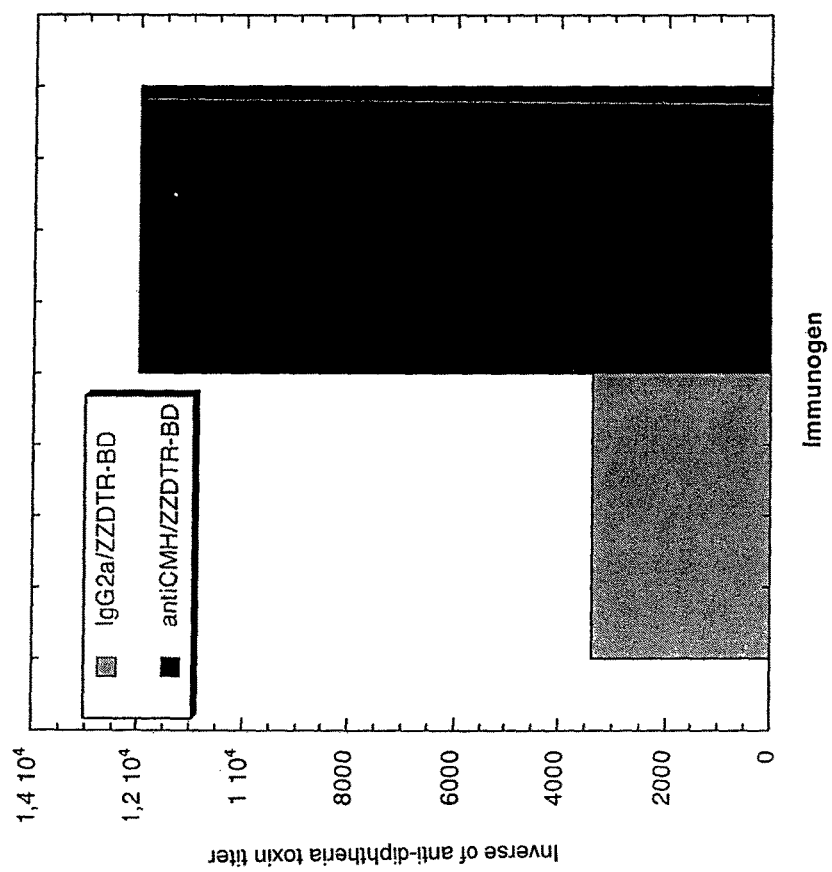
Figure 16:
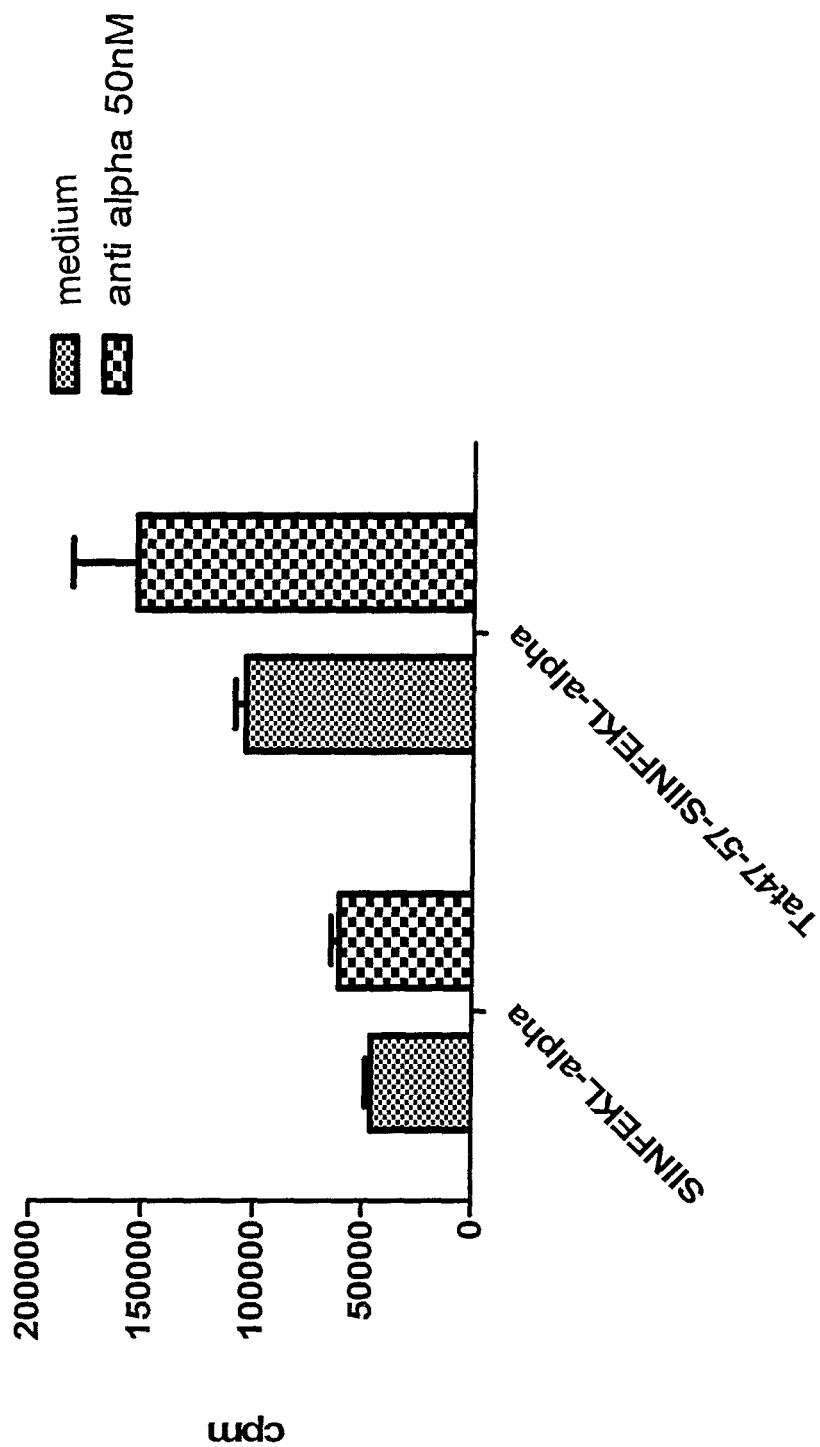
Figure 17:
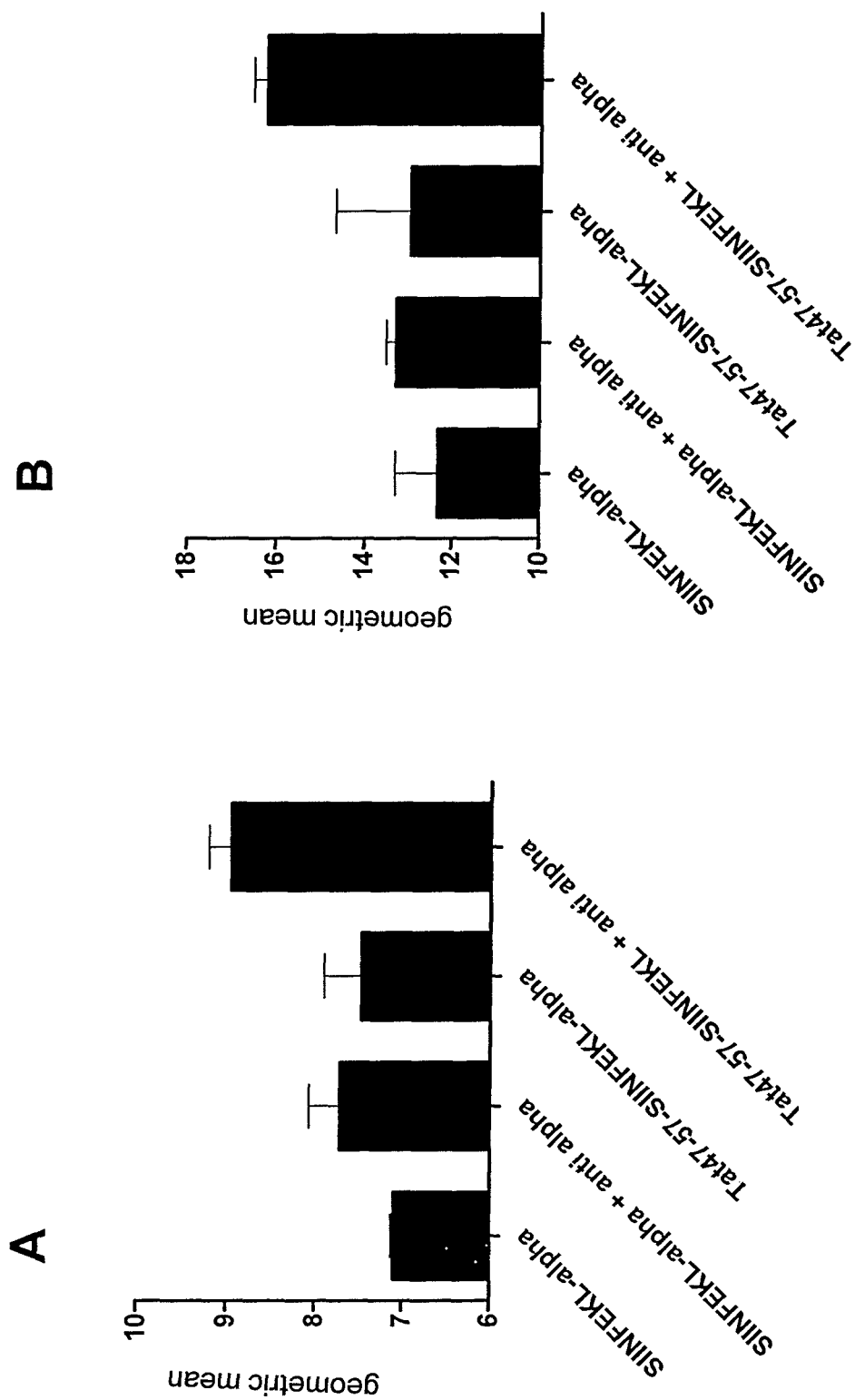

In addition to the above arrangements, the invention also comprises other arrangements which will emerge from the description that follows, which refer to examples of use of the complex which is the subject of the present invention and also to the appended drawings, in which:

FIG. 1 shows the cell binding of Tat101 and of four peptides derived from Tat. A. Sequence of Tat101, Tat101C (22-37)S and of three overlapping peptides. The cysteine-rich (22-37), central (core: 38-48) and basic (49-57) regions are underlined. B, C, D: Cell binding of Tat101 and of four peptides derived from Tat. Series of dilutions of the five peptides were incubated in the presence of, respectively, splenocytes (B), B lymphoma A20 cells (C) and T hybridoma T1B2 cells (D). After incubation for 30 minutes at 4° C., an anti-Tat monoclonal antibody covalently coupled to fluorescein was added and the binding of the peptides to the cells was evaluated by flow cytometry (FACS). Similar results were obtained in two separate experiments;

FIG. 2 shows the binding to various antigen-presenting cells of alpha toxin in free form or in a form coupled to the Tat peptide 37-57. A. Splenocytes were incubated with series of dilutions of alpha toxin (alpha) or alpha37-57, in the presence or absence of an excess of heparin (3 µM). After incubation for 30 minutes at 4° C., a rabbit anti-alpha toxin polyclonal antibody was added. A F(ab)'2 fragment of a goat anti-rabbit IgG polyclonal antibody coupled to fluorescein was added for 30 minutes and the binding of the toxin to the cells was analyzed by FACS. B. Binding to dendritic cells (DCs), analyzed according to the same protocol. C. Binding to A20 cells, analyzed according to the same protocol. Similar results were obtained in at least two separate experiments;

FIG. 3 shows that the capacity of alpha toxin to stimulate T cells is increased when it is coupled beforehand to Tat fragment 37-57 and that the stimulating effect is modified in the presence of an excess of heparin or of 37-57. Splenocytes ($5 \times 10^5$/well) were incubated with serial dilutions of alpha toxin, of alpha toxin plus peptide 37-57, or of alpha37-57, in the presence or absence of an excess (3 µM) of sulfated polysaccharides (heparin, chondroitin A, chondroitin B (A and D). After three hours, T1B2 cells (A) or T1C9 cells (D) were added and the mixtures were incubated for 24 hours. The level of T stimulation which is reflected by IL-2 secretion was evaluated by means of a test for proliferation of an IL-2-dependent CTL line. A similar protocol was used to examine the antigen presentation in the presence or absence of a fixed amount (0.2 µM) of free peptide 37-57 (B and E). A further analysis of the inhibition obtained with peptide 37-57 is shown in C and F. In these experiments, the splenocytes ($10^5$/well) were preincubated at 4° C. for 30 minutes in the presence or absence of peptide 37-57. Alpha37-57 was then added to the wells for one hour at 4° C. The plates were then washed, and the T1B2 (C) or T1C9 (F) cells were added for 24 hours at 37° C. The level of T stimulation which is reflected by IL-2 secretion was evaluated by means of a test for proliferation of an IL-2-dependent CTL line. The results are expressed in cpm (number of counts per minute). Similar results were observed in at least two separate experiments;

FIG. 4 shows that the stimulating effect requires antigen processing. To examine the need for processing, previously fixed splenocytes were incubated for three hours, either with a series of dilutions of alpha toxin, alpha37-57 or peptide 32-49, before the addition of T1B2 (A), or with a series of dilutions of alpha toxin, alpha37-57, peptide Ac24-36 or peptide Ac24-36-Tat37-57 before the addition of T1C9 (B). To compare the stimulating capacities of Ac24-36 and Ac24-36-Tat37-57 in the presence of live APCs, the splenocytes were incubated for 3 hours, with these two peptides, respectively (C). T1C9 was added and the T-cell stimulation was evaluated as described in FIG. 3. Similar results were observed in at least two separate experiments;

FIG. 5 shows that the Tat fragment 37-57 increases the presentation of alpha toxin to T1B2 by B lymphocytes and splenic DCs. The B lymphocytes (A) or the DCs (B) were incubated with serial dilutions of alpha toxin, alpha toxin plus peptide 37-57, or alpha37-57. After three hours at 37° C., the T1B2 cells were added and the T-cell stimulation was evaluated as described in FIG. 3; similar results were obtained in at least two separate experiments;

FIG. 6 shows that the immune complexes containing alpha37-57 bind to A20 cells lacking FcγRII or expressing FcγRII and that the alpha37-57+anti-alpha complex binds the Fcγ receptor type II in a manner similar to alpha+anti-alpha for low antigen concentrations. Serial dilutions of alpha37-57 were incubated overnight in the presence of fixed amounts of a rabbit anti-alpha polyclonal antibody (10 nM or 25 nM). The A20 cells lacking FcγRII (A) or expressing FcγRII (B) were then added to the mixtures and incubated for 30 minutes at 4° C. The cells were then washed and a F(ab)'2 fragment of a goat anti-rabbit IgG polyclonal antibody coupled to fluorescein was added in order to evaluate the binding of the immune complexes by FACS analysis. Similar results were obtained in four separate experiments;

FIG. 7 shows that the alpha37-57+anti-alpha complex exhibits an increased T-stimulating capacity. Series of dilutions of alpha toxin or alpha-37-57 were preincubated overnight at 4° C. in the presence or absence of a fixed amount of anti-alpha rabbit polyclonal antibodies or rabbit IgGs (12.5 nM). The A20 cells lacking FcγRII (A, B) or expressing FcγRII (C, D) were then added. After incubation for 3 hours at 37° C., T1B2 (A, C) or T1C9 (B, D), were added and incubated for 24 hours at 37° C. IL-2 secretion was evaluated using a line of which the growth is dependent on the presence of IL-2. Similar results were obtained in at least two separate experiments;

FIG. 8 shows that the ZZDTR-BD fusion protein is capable of binding heparin and heparan sulfate. Series of dilutions of ZZDTR-BD were incubated in microtitration plates previously adsorbed with heparin coupled to albumin in order to evaluate the capacity of the fusion protein to bind the sulfated sugar (A). The binding to the plates was detected using a rabbit polyclonal antibody and an anti-rabbit antibody goat antibody coupled to peroxydase and a substrate for this enzyme (ABTS). In order to evaluate the specificity of binding to the plates and the region of ZZDTR-BD involved in the interaction, a fixed amount of ZZDTR-BD was incubated in the plates in the presence of series of dilutions of ZZ, Hep6000 and HS, respectively (B). The binding to the plates was detected in the same way as in A;

FIG. 9 shows that the T-stimulating capacity of ZZDTR-BD depends on its ability to bind HSs and immunoglobulins. ZZDTR-BD was preincubated in the presence or absence of an excess of Hep6000 (3 µM), of rabbit IgG (0.8 µM) or of a mixture of Hep6000 (3 µM) and rabbit IgG (0.6 µM). The mixtures were added to A20 cells. After 1 hour at 37° C., the T4B6 hybridoma was added. 24 hours later, the supernatants were removed and the presence of IL-2 was evaluated using an IL-2-dependent CTL line;

FIG. 10 shows the determination of the splenocyte population bound by ZZDTR-BD. A fixed amount of this complex was incubated in the presence or absence of splenocytes and of three phycoerythrin-labeled antibodies specific for CD4+ T lymphocytes (anti-CD4-PE), for CD8+ T lymphocytes (anti-CD8-PE) and for B lymphocytes (anti-CD19-PE). After 30 minutes at 4° C., the cells were washed and incubated in the presence of an anti-rabbit antibody polyclonal antibody coupled to fluorescein. 30 minutes later, the cells were washed and analyzed by flow cytometry;

FIG. 11 shows that the T-stimulating capacity of ZZDTR-BD is increased when it is complexed beforehand with antibodies specific for determinants expressed at the surface of APCs. ZZDTR-BD was preincubated in the presence or absence of equimolar amounts of the 14-4-4S antibody, the 10-1.D.2 antibody and the Mα2-3 antibody, respectively. The mixtures were added to A20 cells or to splenocytes. After 1 hour at 37° C., the T4B6 hybridoma was added. 24 hours later, the supernatants were removed and the presence of IL-2 was evaluated using an IL-2-dependent CTL line;

FIG. 12 shows the binding of the alpha/anti-alpha and alpha37-57/anti-alpha complexes to BALB/c mouse splenocytes, analyzed by flow cytometry using an F(ab)'2 fragment of a goat anti-rabbit IgG polyclonal antibody coupled to fluorescein. Cal FITC: splenocytes (control). Alpha/anti-alpha: splenocytes+alpha/anti-alpha immune complexes. Alpha37-57/anti-alpha: splenocytes+alpha37-57/anti-alpha immune complexes;

FIG. 13 shows the determination of the splenocyte population bound by the anti-alpha toxin/alpha toxin37-57 complex. A fixed amount of this complex was incubated in the presence or absence of splenocytes and of three phycoerythrin-labeled antibodies specific for CD4+ T lymphocytes (anti-CD4-PE), for CD8+ T lymphocytes (anti-CD8-PE) and for B lymphocytes (anti-CD19-PE). After 30 minutes at 4° C., the cells were washed and incubated in the presence of an anti-rabbit antibody polyclonal antibody coupled to fluorescein. 30 minutes later, the cells were washed and analyzed by flow cytometry;

FIG. 14 shows the determination of the splenocyte population bound by the 14-4-4S/ZZDTR-BD complex. A fixed amount of ZZDTR-BD or of the 14-4-4S/ZZDTR-BD complex was incubated in the presence or absence of splenocytes and of three phycoerythrin-labeled antibodies specific for CD4+ T lymphocytes (anti-CD4-PE), for CD8+ T lymphocytes (anti-CD8-PE) and for B lymphocytes (anti-CD19-PE). After 30 minutes at 4° C., the cells were washed and incubated in the presence of an anti-rabbit antibody polyclonal antibody coupled to fluorescein. 30 minutes later, the cells were washed and analyzed by flow cytometry;

FIG. 15 shows that the anti-MHC/ZZDTR-BD complex induces, in the absence of adjuvant, an anti-diphtheria toxin antibody response which is greater than that induced by the IgG2a/ZZDTR-BD complex. The two complexes were respectively injected in the absence of adjuvant into two groups of four BALB/c mice. The animals were taken forty-five days after the immunization and the sera were pooled. The presence of anti-diphtheria toxin antibodies was evaluated by immunoenzymatic assay;

FIG. 16 shows that a compound having the ability to target HSs and a molecule expressed specifically at the surface of APCs is capable of inducing a greater cytotoxic immune response than a compound which targets only HSs or only the molecule specifically expressed at the surface of APCs. The Tat47-57-SIINFEKL-alpha and SIINFEKL-alpha proteins (final dilution 1 μM), complexed or not complexed with the anti-alpha toxin rabbit polyclonal antibody (anti-alpha, 50 nM) were added to JAWS II dendritic cells used as ACPs. After 5 h at 37° C., the cells were fixed and OT1 mouse splenocytes, which contain CD8+ T lymphocytes that recognize the T epitope, of sequence SIINFEKL, in association with class I molecules of type I-A$^b$, were added. The level of CD8+ T stimulation of the OT1 splenocytes was evaluated by means of a cell proliferation test. The results are expressed in cpm (number of counts per minute);

FIG. 17 shows that a compound which has the ability to target HSs and a molecule expressed specifically at the surface of APCs increases the expression of the CD80 and CD86 co-stimulatory molecules more strongly than compounds which target only HSs or only the molecule specifically expressed at the surface of APCs. The wild-type alpha toxin and the Tat47-57-SIINFEKL-alpha and SIINFEKL-alpha proteins (final concentration 1 μM) complexed or not complexed with the antibody (25 nM final concentration) were added to JAWS II dendritic cells used as APCs. After 24 hours at 37° C., the cells were washed, incubated in the presence of fluorescein-labeled anti-CD80 (A) and anti-CD86 (B) antibodies, and the binding of the antibodies to the cells was analyzed by flow cytometry.

EXAMPLE 1

Selection of a Tat Fragment Capable of Binding Cell-Surface Heparan Sulfates and Coupling to Alpha Toxin 1. Materials and Methods 1.1 Synthesis of Tat Peptides The Tat protein (SEQ ID NO: 8; FIG. 1A) corresponds to that of the NDK isolate of HIV-1 (Groenink et al., J. Virol., 1991, 65, 1968-175) which represents the consensus sequence obtained from 66 sequences of primary isolates of HIV-1 reported in the SWISSPROT and TrEMBL databases between 1999 and 2000. The chemical synthesis of the Tat peptides was carried out by means of the Fmoc/tert-butyl strategy using an Applied Biosystems 433A automatic peptide synthesizer. The chemical process uses 0.1 mmol of Fmoc-Asp(OtBu)-PAL-PEG-PS resin, a 10-fold excess of each amino acid, dicyclohexylcarbodiimide/1-hydroxy-7-azabenzotriazole and diisopropylethylamine/N-methylpyrrolidone. The cleavage and the deprotection were carried out using a trifluoroacetic acid/triisopropylsilane/water mixture (9.5/0.25/0.25, v/v/v). The raw material was precipitated twice with tert-butyl methyl ether cooled to 4° C. and then dissolved in a 15% aqueous acetic acid solution. The peptides were then purified by reverse-phase high performance liquid chromatography (HPLC), on a Vydac C18 column (Hesperia). The peptides and the proteins synthesized were characterized by mass spectrometry and by amino acid analysis. They are stored at 20° C., in lyophilized form.

1.2 Coupling of the Tat$_{37-57}$ Peptide to Alpha Toxin

The alpha toxin of *Naja nigricollis* (Swiss-Prot P01468; SEQ ID NO: 9) was purified as described in Fryklund et al., Biochemistry, 1975, 14, 2865-2871. Alpha toxin monothiolate, comprising an N-terminal thiol group, was obtained using N-succinimidyl 3-(2-pyridyldithiol)propionate (SPDP) as bifunctional reagent, according to the protocol previously described (Léonetti et al., J. Exp. Med., 1999, 189, 12177-). The additional disulfide bridge was then reduced using an acetate buffer, pH 4.5, containing 0.1 M NaCl and 25 mM dithiothreithiol. The mixture was then stirred at ambient temperature for 20 min and the solution was filtered on a PD10 column equilibrated with 0.1 M phosphate buffer, pH 6.1, containing 0.1 M NaCl. The toxin monothiolate eluted from the dead volume was then incubated for 1 hour at ambient temperature in the presence of a three-fold excess of the $Tat_{37-57}$ peptide, in PBS buffer. The mixture was then filtered on a PD10 column equilibrated with 0.1M phosphate buffer, pH 7, the purity of the conjugate was evaluated by reverse-phase high performance liquid chromatography (HPLC).

1.3 Cell Binding

Cells Used

The murine B lymphoma line called A20, obtained as described in K. J. Kim et al., J. Immunol., 1979, 122, 549-, is available under No. ATCC TIB-208.

The T hybridoma, specific for α toxin and for erabutoxin a, called T1B2, was obtained as described in B. Maillère et al., J. Immunol, 1993, 150, 5270-.

The mouse splenocytes were isolated from mouse spleens. For this, the animals were sacrificed and then the spleens were removed sterilely. The spleens were dilacerated and the red blood cells were lysed at 4° C. using a Gey's buffer. The splenocytes were recovered after centrifugation for 10 minutes at 4° C.

The dendritic cells were isolated from mouse splenocytes using MACS microbeads, according to the protocol of the manufacturer (Miltenyi Biotec). Briefly, the spleens were incubated in the presence of collagenase D (2 mg/ml) for 30 minutes at 37° C. in the presence of an excess of nonspecific mouse IgGs. The cells were then incubated at 4° C. Fifteen minutes later, anti-CD11c microbeads were added and incubated for 15 minutes at 6-8° C. The splenocytes were washed, centrifuged and passed through magnetic columns. The enrichment was evaluated by FACS analysis, using four anti-CD antibodies (anti-CD4-FITC, anti-CD19-PE, anti-CD11c-FITC and anti-IA/IE-PE, Becton-Dickinson). The purity was greater than 95%.

Cell Binding of Tat101 and of Tat Peptides with Different C-Terminal Extensions

Series of dilutions of each Tat peptide were incubated in the presence of various types of cells ($2\times10^5$ splenocytes per well, $10^5$ A20 or T1B2 cells per well) for 30 min at 4° C. in PBS buffer/0.5% BSA. The cells were washed three times and incubated in the presence of a murine monoclonal antibody specific for the N-terminal region of Tat, covalently coupled to fluorescein, as described in Lecoq et al., Vaccine 2008, 26, 2615-2626 (1 μg/well). After incubation for 30 min at 4° C., the cells were washed and analyzed by FACS®.

Cell Binding of Alpha Toxin in Free Form or Covalently Coupled to $Tat_{37-57}$ (Alpha37-57)

Series of dilutions of alpha toxin and alpha37-57 were incubated in the presence of various cell types ($2\times10^5$ splenocytes per well, $10^5$ A20 cells or $10^5$ dendritic cells) for 30 min at 4° C. in PBS buffer/0.5% BSA. The cells were washed and incubated in the presence of a rabbit anti-alpha toxin polyclonal antibody (1 μg/well). After incubation for 30 min at 4° C., the cells were washed and an F(ab)'2 fragment of a goat anti-rabbit IgG polyclonal antibody coupled to fluorescein was added. After incubation for 30 min at 4° C., the cells were washed and analyzed by FACS®.

2. Results

Tat is a heparin-binding protein (Albini et al., Oncogene, 1996, 12, 289-; Rusnati et al., J. Biol. Chem., 1997, 272, 11313-) which is internalized in cells via a mechanism requiring heparan sulfate proteoglycans (HSPGs) at the surface of the cells (Tyagi et al., J. Biol. Chem., 2001, 276, 3254). A wild-type Tat protein of 101 residues (Tat101) and four Tat-derived peptides were produced by chemical synthesis in order to select a monomeric Tat fragment capable of binding the cells (FIG. 1A).

In these derivatives, the seven cysteine residues of Tat located in the cysteine-rich region of the molecule (amino acids 22 to 37) were replaced with seven serines, given that Tat has a natural tendency to form a large variety of disulfide-bridge-mediated oligomers (Kittiworakarn et al., J. Biol. Chem., 2006, 281, 3105-). The first derivative is a complete molecule called Tat101C(22-37)S (Kittiworakarn et al., J. Biol. Chem., 2006, 281, 3105-). The other three polypeptides are C-terminal-truncated Tat fragments (1-57C (22-37)S, 1-48C(22-37)S, 1-37C(22-37)S). After having evaluated the purity of the five polypeptides, their ability to bind various cell types was compared. In these experiments, the cell binding was revealed using a monoclonal antibody directed against the N-terminal region of Tat and flow cytometry analysis (FACS).

FIG. 1B shows that Tat 101 binds splenocytes, whereas Tat101C(22-37)S interacts weakly, indicating that the cysteine-rich region plays an important role in the interaction of Tat with cells. Unlike Tat101C(22-37)S, the 1-57C(22-37)S peptide binds splenocytes like wild-type Tat101, indicating that the loss of binding due to the absence of the cysteine residues has been counterbalanced by the absence of region 58-101. It requires approximately 50 times more 1-48C(22-37)S peptides to obtain binding similar to that of the 1-57C(22-37)S peptide, indicating that the absence of residues 49 to 57, corresponding to the basic region of Tat, greatly decreases the binding capacity. Finally, no binding was observed with the 1-37C(22-37)S peptide, showing that the interaction is abolished in the absence of residues 38 to 48 corresponding to the core domain of Tat.

Similar results were obtained using the murine B lymphoma cells of the A20 line (FIG. 1C) or cells of the T hybridoma called T1B2 (FIG. 1D), indicating that Tat and fragments thereof are capable of binding a variety of cells, in accordance with the ubiquitous distribution of HSPGs. Owing to these results which show the involvement of the cysteine-rich (residues 22-37), core (residues 38 to 48) and basic residue-rich (residues 49-57) regions in cell binding, and the prior observations that Tat has a spontaneous propensity to form a large variety of disulfide-bridge-mediated oligomers (Kittiworakarn et al., J. Biol. Chem., 2006, 281, 3105-), only the basic residue-rich and core regions were selected for preparing a homogeneous monomeric fragment capable of binding cells. Cystein 37 of Tat was incorporated into this fragment in order to couple the alpha toxin of *Naja nigricollis* (That et al., J. Biol, Chem., 2004, 279, 50257-). The new peptide synthesized, called 37-57, was coupled to alpha toxin via a disulfide bridge between cysteine 37 and a thiol group previously incorporated onto leucine 1 of the alpha toxin (Kessler et al., Bioconjug. Chem., 1994, 5, 199-), since this residue is remote from the T epitopes of the toxin that are recognized by the H-2d haplotype (Léonetti et al., J. Immunol., 1990, 145, 4214-; Maillère et al., J. Immunol., 1993, 150, 5270). The derivative was called alpha37-57.

In order to study whether the peptide 37-57 confers on alpha toxin the ability to bind cells, various dilutions of alpha toxin or of alpha37-57 polypeptide were incubated in the presence, respectively, of splenocytes, of A20 cells or of dendritic cells. After incubation for 30 min at 4° C., a rabbit anti-alpha toxin polyclonal antibody and an F(ab)'2 fragment of a goat anti-rabbit IgG polyclonal antibody coupled to fluorescein were added, and then the analysis by FACS was carried out.

FIG. 2 shows that the alpha37-57 polypeptide increases the fluorescence intensity of various cell types, whereas free alpha toxin (alpha) is not very effective, strongly suggesting that peptide 37-57 confers, on alpha toxin, the ability to bind cells. In order to reinforce the role of Tat portion 37-57 in cell binding, the cell binding of alpha37-57 was also examined in the presence of heparin, a soluble sulfated polysaccharide, representative of heparan sulfates and capable of binding Tat (Albini et al., Oncogene, 1996, 12, 289). The fluorescence intensity decreases when the splenocytes are preincubated in the presence of alpha37-57 and of an excess of heparin (FIG. 2A), demonstrating that the binding of alpha37-57 is mediated by the Tat portion.

EXAMPLE 2

Alpha Toxin is Presented More Effectively to Two Alpha-toxin-Specific T-cell Hybridomas when it is Covalently Coupled to Peptide 37-57

1. Materials and Methods
1.1 Isolation of B Lymphocytes and of Dendritic Cells from Splenocytes The dendritic cells were isolated as described in example 1. The B lymphocytes were isolated using anti-CD19 microbeads according to a similar protocol.
1.2 T-cell Stimulation Tests All the experiments were carried out using DCCM1 (Biological Industries) as synthetic culture medium. Serial dilutions of the various antigens were incubated in the microculture wells (Nunc) for 3 hours at 37° C. in the presence, either of A20 ($5 \times 10^4$/well), or of splenocytes ($5 \times 10^5$/well) or of DCs ($3 \times 10^4$/well). An alpha-toxin-specific T-cell hybridoma (T1C9: Maillère et al., Mol. Immunol., 1995, 32, 1073-; T1B2: Maillère et al., J. Immunol., 1993, 150, 5270-; $5 \times 10^4$/well) was then added to the wells and the cells were then cultured for 24 h at 37° C. The level of T stimulation which is reflected by IL-2 secretion was evaluated by sampling the culture supernatants and measuring the presence of IL-2 using a cytotoxic T-cell (CTL) line of which the growth is dependent on this interleukin, as described in Gillis et al., Nature, 1977, 268, 154-156. The proliferation of the IL-2-dependent CTL line was evaluated by measuring the incorporation of tritiated methyl-thymidine (5 Ci/mmol). The data are expressed in cpm.
2. Results The presentation of alpha37-57 and of free alpha toxin to two specific T-cell hybridomas, called T1B2 and T1C9, which recognize respectively a thiol-dependent epitope (Maillère et al., J. Immunol., 1993, 150, 5270-) and a thiol-independent epitope (Maillère et al., Mol. Immunol., 1995, 32, 1073-) was evaluated using splenocytes as antigen-presenting cells (APCs). As shown in FIG. 3A, the amount of free alpha toxin required to stimulate T1B2 is similar in the presence and in the absence of equimolar amounts of free peptide 37-57, thereby indicating that this free Tat fragment has no influence on antigen presentation. On the other hand, 5-fold smaller amounts of alpha37-57 are sufficient to stimulate T-cell hybridomas as effectively as free alpha toxin, indicating that the increase in capacity for stimulating T cells is due to the covalent coupling to the Tat peptide. Two observations indicate that the stimulating effect is due to the targeting of the hybrid protein onto the HSPGs expressed at the surface of the APCs. The first observation was made using three different sulfated soluble polysaccharides incubated in excess (3 µM) with serial dilutions of alpha and of alpha37-57. Neither chondroitin A nor chondroitin B, which are representatives of chondroitin sulfates and which bind Tat weakly (Rustani et al., J. Biol. Chem., 1997, 272, 11313-), are capable of influencing the stimulating effect (FIG. 3A). On the other hand, heparin, which is representative of heparan sulfates and is capable of inhibiting the binding of the alpha37-57 hybrid to splenocytes (FIG. 2A), is capable of decreasing the T-stimulating capacity of alpha37-57 at the level observed with free alpha toxin. The second observation was made using excess amounts of free peptide 37-57. In a first series of experiments carried out with a protocol similar to that used for the sulfated polysaccharides, free peptide 37-57 has no effect on the presentation of free alpha toxin. Indicating that it is not toxic at the concentration used (0.2 µM) and that it weakly, or even not at all, inhibits the presentation of alpha37-57 (FIG. 3B). However, this weak inhibition capacity is linked to the protocol used, given that an important impairment of the T-stimulating capacity was observed when the cell-binding step was separated from that of processing and presentation (FIG. 3C). Thus, the stimulation of the T-cell hybridoma is decreased when the splenocytes are incubated at 4° C. with peptide 37-57 and alpha37-57 and they are subsequently washed to remove the unbound protein before the addition of the T1B2 cells. These observations were also made when the antigen presentation was studied by means of the T1C9 hybridoma (FIGS. 3D, 3E, 3F). Thus, the hybrid protein is 13 times more powerful than alpha toxin in terms of stimulating T1C9, and this phenomenon is affected in the presence of an excess of heparin (FIG. 3D) or of free peptide 37-57 (FIG. 3F). Consequently, the stimulating effect is not associated with a particular epitope. Since alpha toxin is a very stable protein (That et al., J. Biol. Chem., 2004, 279, 50527-) which absolutely requires processing in order to stimulate T cells (Maillère et al., J. Immunol., 1993, 150, 5270-), it was subsequently examined whether the stimulating effect was dependent on antigen processing. To do this, fixed splenocytes were used as APCs. In their presence, the two T-cell hybridomas are not stimulated by alpha toxin nor by alpha37-57 (FIGS. 4A and 4B). This absence of stimulation is not due to an impairment of the presentation capacity of the fixed splenocytes, given that they remain capable of presenting peptide 32-49 and peptide Ac24-36 to the T1B2 (FIG. 4A) and T1C9 (FIG. 4B) hybrodomas, respectively. These results therefore indicate that the increase in T-stimulating capacity is dependent on processing of the toxin by the APCs. Next, it was evaluated whether Tat fragment 37-57 can also increase the presentation of an antigen which does not require processing. When comparing the stimulating capacity of peptide Ac24-36 in its free form or its form coupled beforehand to Tat37-57, it was observed that Ac24-36 and Ac24-36-Tat37-57 do not significantly differ in terms of their ability to stimulate T1C9, in the presence of fixed (FIG. 4B) or live (FIG. 4C) splenocytes, indicating that the stimulating effect is not linked to an increase in presentation at the surface of the cells. All of these results indicate that the Tat37-57 fraction targets HSPGs and thus increases MHC class II-restricted presentation of a protein antigen which requires processing. A similar increase in T-stimulating capacity was observed when alpha toxin is coupled to the basic region of Tat.

Next, the lymphocytes and the DCs were purified from splenocytes in order to examine whether the stimulating effect is observed in the presence of these two different types of APCs. With the B lymphocytes, the stimulation of T1B2 requires an amount of alpha37-57 which is approximately 10 times less than that of free alpha toxin, or of free alpha toxin plus peptide 37-57 (FIG. 5A). With the DCs, the effect is more pronounced, since the T-cell stimulation requires 180 times less hybrid than free alpha toxin in the presence or absence of peptide 37-57 (FIG. 5B). Consequently, the stimulating effect is observed in the presence of these two types of APCs and is dependent on covalent coupling of the Tat fragment to the protein antigen.

EXAMPLE 3

APCs Bearing an Fcγ Receptor Type II (FcγRII) More Efficiently Present an Immune Complex Containing an Antigen Covalently Coupled to Peptide 37-57

1. Materials and Methods
Cells Used
See example 1.
The A20 B lymphoma lines lacking or expressing FcγRII are described in Amigorena et al., Science, 1992, 256, 1808-.
Binding of Immune Complexes to Cells
Series of dilutions of alpha toxin or of alpha37-57 were incubated overnight at 4° C., in the presence of a rabbit anti-alpha toxin polyclonal antibody (10 nM or 25 nM). The A20 cells and A20 cells expressing FcγRII were then added ($10^5$ per well) and incubated for 30 min at 4° C. in PBS buffer supplemented with 0.5% bovine serum albumin (PBS/0.5% BSA). The mixtures were then washed and a goat anti-rabbit IgG antibody coupled to fluorescein was added. After incubation for 30 min at 4° C., the cells were washed and analyzed by FACS®.

T-cell Stimulation Tests

See example 2.

Serial dilutions of alpha or of alpha37-57 in the presence or absence of anti-alpha (12.5 nM) or of rabbit antibody not specific for the toxin (called rabbit IgG) were preincubated overnight at 4° C. A20 cells lacking or expressing FcγRII ($5\times10^4$ cells per well) were added. After incubation for 3 hours at 37° C., the T1B2 and T1C9 hybridomas were respectively added in a proportion of $5\times10^4$ cells per well. After culture for 24 hours at 37° C., the level of T stimulation which is reflected by IL-2 secretion was evaluated by sampling the culture supernatants and measuring the presence of IL-2 using a CTL line of which the growth is dependent on this interleukin. The proliferation of the IL-2-dependent CTL line was evaluated by measuring the incorporation of tritiated methyl thymidine (5 Ci/mmol).

2. Results

Since HSPGs can act as coreceptors which modulate the meeting between extracellular proteins and their receptors by forming heparan sulfate (HS)/protein complexes (Park et al., J. Biol. Chem., 2000, 275, 29923-; Carey, D. J. Biochem. J., 1997(Pt1):1), alpha37-57 was used to study whether HSPGs can regulate receptor-mediated antigen presentation. The present study concerns presentation mediated by the Fcγ receptor type II (FcγRII) given that this receptor binds immune complexes (ICs) and it influences antigen presentation (Sallusto et al., J. Exp. Med., 1994, 179, 1109; Amigorena et al., Science, 1992, 256, 1808-; Amigorena et al., J. Exp. Med., 1998, 187, 505-; Regnault et al., J. Exp. Med., 1999, 189, 371-). Consequently, an immune complex was used. This complex contains a rabbit anti-alpha toxin polyclonal antibody (anti-alpha) and the alpha toxin from *Naja nigricollis* which has been coupled beforehand to Tat fragment 37-57 capable of binding HSs (alpha37-57). This immune complex, called alpha37-57+anti-alpha, therefore has the ability to bind, firstly, HSs expressed at the surface of most cells, and, secondly, receptors which recognize the antibody Fc region and which are selectively expressed at the surface of APCs.

This complex was evaluated using, as APCs, the A20 B lymphoma line lacking or expressing the Fcγ receptor type II (FcγRII; Amigorena et al., Science, 1992, 256, 1808-). Alpha37-57+anti-alpha was compared with a complex lacking the 37-57 region, called alpha+anti-alpha, in order to evaluate what is provided by the region capable of binding HSs. Two characteristics were studied: firstly, the capacity for binding two types of A20 cells, secondly the capacity for stimulating two T hybridomas, called T1C9 and T1B2, which are specific for alpha toxin.

2.1 Capacity for Binding A20 Cells Lacking or Expressing FcγRII: For Low Antigen Concentrations, the Alpha37-57+Anti-alpha and Alpha37-57+Anti-Alpha Complexes Bind the Fcγ Receptor Type II in a Similar Manner The binding of the two complexes to A20 cells was evaluated (FIG. 6). As can be seen in FIG. 6A, the A20 cells which do not express FcγRII are bound only by the alpha37-57+anti-alpha complex, thereby indicating that the interaction of the complex is mediated by the HS-binding 37-57 region. The scenario is different in the presence of the A20 cells expressing FcγRII (FIG. 6B). Indeed, the alpha+anti-alpha complex binds to the cells in a manner similar to alpha37-57+anti-alpha for Ag concentrations less than or equal to 1 nM, thereby indicating that, for low antigen concentrations, the two complexes both bind the cells. These observations therefore indicate that the two complexes interact similarly with FcγRII expressed at the surface of the A20 cells, thereby indicating that the presence of the HS ligand does not disrupt the interaction of the antibodies with FcγRII. When the amount of antigen becomes greater than 1 nM, the interaction of alpha+anti-alpha decreases, thereby indicating that the antibodies bind less efficiently the FcγRIIs expressed at the surface of the cells. On the other hand, the binding of alpha37-57+anti-alpha increases, thereby indicating that the interaction with the cells becomes mainly mediated by the 37-57 region.

2.2 T-simulating Capacity: The T-stimulating Capacity of Alpha Toxin is Increased when the Protein is Coupled to 37-57 and Complexed with the Anti-Alpha Antibody The T-stimulating capacity of the alpha+anti-alpha and alpha37-57+anti-alpha complexes was evaluated (FIG. 7). As can be seen in this figure, the A20 cells negative (FIG. 7A) and positive (FIG. 7C) for FcγRII present alpha37-57 to the T1B2 hybridoma better than they present alpha to the T1B2 hybridoma, thereby indicating that the presence of the HS ligand increases presentation of the protein and its T-stimulating capacity. In the presence of A20 cells lacking FcγRII, the presentation of the alpha37-57+anti-alpha immune complex remains similar to that of free alpha37-57 and the presentation of the alpha+anti-alpha complex remains similar to that of alpha (FIGS. 7A and 7B), thereby indicating that the T-stimulating capacity of the antigen (Ag) is not modified when it is associated with the antibody and presented by these APCs. The result is similar for the alpha+anti-alpha complex in the presence of A20 cells expressing FcγRII (FIGS. 7C and 7D), thereby indicating that the T-stimulating capacity of the wild-type alpha toxin is not modified when it is associated with the antibody which interacts with the Fc receptor expressed at the surface of the APCs. The result is, on the other hand, substantially different for the alpha37-57+anti-alpha complex. Indeed, the T-stimulating capacity of alpha37-57 is greatly increased when it interacts beforehand with anti-alpha (FIGS. 7C and 7D). Thus, to stimulate T1B2 with alpha37-57+anti-alpha, amounts of Ag that are respectively 130 times lower than free alpha37-57 (alpha+rabbit IgG), and more than 1000 times lower than free alpha (alpha+rabbit IgG) or complexed with anti-alpha (alpha+anti-alpha), are sufficient. The same phenomenon is observed for the T1C9 hybridoma, thereby indicating that the increase in T-stimulating capacity is provided for all the T epitopes of alpha toxin. These results therefore indicate that the targeting of FcγRII makes it possible to increase the T-stimulating capacity of alpha toxin complexed with the antibody only in the case where it is coupled beforehand to the 37-57 fragment. Furthermore, the increase in the T-stimulating capacity disappears when the complex is incubated in the presence of an excess of heparin (see alpha37-57+anti-alpha+heparin, FIG. 7D), thereby indicating that the 37-57 fragment contributes to the effect.

All these observations therefore indicate that the T-stimulating capacity of alpha toxin is increased when it is associated with an HS ligand and with an Fcγ receptor II ligand, and that this phenomenon is brought about by the targeting of FcγRII in combination with the capacity for binding HSs.

EXAMPLE 4

The Diphtheria Toxin Domain Capable of Binding to the Cell Receptor is Capable of Binding Heparan Sulfates Fusion proteins incorporating, firstly, an antigenic protein and, secondly, a ZZ double domain derived from *Staphylococcus aureus* protein A have been previously constructed (Léonetti et al., J. Immunol, 1998, 160, 3820-). ZZ can bind to immunoglobulins in a manner similar to protein A and it has been shown that fusion proteins of ZZAg type have an increased T-stimulating capacity. It has been shown that this increase is mediated by the ZZ region which binds APCs bearing immunoglobulins and thus increases the amount of Ag incorporated into the cells. This fusion protein system therefore enables surface-immunoglobulin-mediated Ag targeting. On the basis of this system, another fusion protein, called ZZDTR in the publication by Lobeck et al. (Infection and Immunity, 1998, 66, 418-423), was constructed. This fusion protein, now called ZZDTR-BD, contains the diphtheria toxin domain (DTR-BD) capable of binding the cell receptor which is the target of this toxin. This receptor is not expressed at the surface of APCs. It was evaluated whether the ZZDTR-BD fusion protein was capable of binding heparan sulfates.

The binding of ZZDTR-BD to heparan sulfates was evaluated in two steps.

In a first step, the binding of ZZDTR-BD to microtitration plates bearing heparin was evaluated. For this, the microtitration plates were pre-adsorbed with heparin-albumin (1 μg/100 μl/well) and then saturated with bovine serum albumin (200 μl/well at 0.3%). The plates were then washed and a series of dilutions of ZZDTR-BD was deposited in the wells and incubated overnight at 4° C. The plates were washed and a rabbit polyclonal antibody was added. After 30 minutes at ambient temperature, the plates were washed and an anti-rabbit antibody goat antibody was added. 30 minutes later, the plates were washed, a substrate was added, and the coloration was measured at 414 nm after incubation for 30 minutes.

In a second step, it was evaluated whether the binding of ZZDTR-BD to the plates adsorbed with heparin-albumin can be modified when the fusion protein is incubated in the presence of solutions containing either a heparin fragment having a molecular weight of 6000 Da (Hep6000), or heparan sulfate or ZZ. For this, a fixed concentration of ZZDTR-BD was deposited in the presence of series of dilutions of Hep6000, of heparan sulfate (HS) or of ZZ. After incubation overnight at 4° C., the plates were washed and a rabbit polyclonal antibody was added. After 30 minutes at ambient temperature, the plates were washed and an anti-rabbit antibody goat antibody was added. 30 minutes later, the plates were washed, a substrate was added and the coloration was measured at 414 nm after incubation for 30 minutes.

As can be seen in FIG. 8A, ZZDTR-BD binds the plates adsorbed with heparin-albumin, thereby indicating that the fusion protein is capable of interacting with this sulfated sugar which is similar to heparan sulfates. The interaction of ZZDTR-BD with the plates is inhibited by the solutions of Hep6000 and of HS, thereby indicating that the fusion protein interacts with HSs and heparin using a common site. However, this site is not located in the ZZ region, since the free ZZ double domain does not modify the binding of ZZDTR-BD to the plates. It can therefore be concluded therefrom that the HS-binding capacity is mediated by the DTR-BD domain of ZZDTR-BD.

EXAMPLE 5

The ZZDTR-BD Fusion Protein has a T-stimulating Capacity which is Influenced by its Ability to Bind HSs and Immunoglobulins Expressed at the Surface of APCs Since the fusion protein is capable of binding HSs and immunoglobulins expressed at the surface of APCs, it was evaluated whether its T-stimulating capacity is dependent on these two characteristics. For this, the presentation of ZZDTR-BD to a diphtheria-toxin-specific T hybridoma was studied "in vitro". The hybridoma, called T4B6, recognizes the 92-106 T epitope located in the DTR-BD domain of diphtheria toxin.

To evaluate the T-stimulating capacity, series of dilutions of ZZDTR-BD in the presence or absence of an excess of Hep6000 (3 μm final concentration), of HS (3 μM final concentration) or of rabbit IgG (0.8 μM final concentration) were incubated for 3 h at 4° C. in cell culture plates. The A20 line, which is a B lymphoma that has surface immunoglobulins ($5 \times 10^4$ cells/well, FIG. 9) and has presentation capacities, was then added. After incubation for 1 hour at 37° C., the T4B6 hybridoma is added and the mixture is incubated for 24 hours at 37° C. The stimulation of the hybridoma is then evaluated by measuring the presence of IL-2 in the supernatants. For this, the supernatants are sampled and incubated in the presence of a CTL line of which the growth is dependent on the presence of IL-2. The cell growth is evaluated by measuring the incorporation of tritiated thymidine into the IL-2-dependent CTL line.

As can be seen in FIG. 9, in the presence of the A20 B lymphoma, ZZDTR-BD is capable of stimulating the diphtheria-toxin-specific T4B6 hybridoma. The stimulation is weaker when ZZDTR-BD is incubated beforehand in the presence of an excess of Hep6000, thereby demonstrating that the T-stimulating capacity of the protein is influenced by its ability to bind heparin. Since it has been previously shown that the ZZAg fusion protein system enables targeting of Ags to immunoglobulins expressed at the surface of APCs (Léonetti et al., J. Immunol., 1998, 160, 3820-), these results demonstrate that ZZDTR-BD has a T-stimulating capacity which is increased by its capacity for binding immunoglobulines and compounds of the heparan sulfate family.

In order to determine the population of splenocytes bound by ZZDTR-BD, a fixed amount of ZZDTR-BD (10 nM) was incubated in the presence of splenocytes and of three antibodies respectively specific for CD4+ T lymophocytes (anti-CD4), for CD8+ T lymphocytes (anti-CD8) and for B lymphocytes (anti-CD19). These three antibodies are labeled with phycoerythrin. After 30 minutes at 4° C., the cells were washed and incubated in the presence of a rabbit polyclonal antibody which can interact with the ZZ region of the fusion protein. 30 minutes later, an anti-rabbit antibody polyclonal antibody coupled to fluorescein was added. After incubation for 30 minutes at 4° C., the cells were washed and analyzed by flow cytometry. As can be seen in FIG. 10, the splenocytes contain approximately 14% CD8+ T lymphocytes, and 22% of these cells are bound by ZZDTR-BD. The splenocytes contain approximately 32% of CD4+ T lymphocytes, and 15.8% of these cells are bound by ZZDTR-BD. The splenocytes contain approximately 52% B lymphocytes, and 51.5% of these cells are bound by ZZDTR-BD. Since the B cells express surface antibodies and the CD4+ T and CD8+ T cells are devoid of antibodies, it may be concluded that ZZDTR-BD targets the surface antibodies and thus preferentially binds to B lymphocytes, which are APCs.

EXAMPLE 6

Increase in the T-Stimulating Capacity of the ZZDTR-BD Fusion Protein Associated Beforehand with Antibodies Specific for APC Surface Determinants Protein A and the Z domain which is derived therefrom can bind to the Fc region of various classes of antibodies. It has previously been shown that this characteristic can be exploited to form complexes between Abs and fusion proteins of ZZAg type (Léonetti et al., J. Immunol., 1998, 160, 3820-). It has also been shown that an Ab/ZZAg complex containing an Ab specific for an APC surface determinant is presented better to T cells than free ZZAg or ZZAg complexed with a nonspecific antibody, and that it is capable of inducing, in animals, an immune response in the absence of adjuvant. The same principle of formation of complexes between ZZDTR and antibodies was therefore used to evaluate whether the fusion protein which has the capacity for binding HSs can thus experience an increase in its T-stimulating capacity when it interacts with antibodies capable of targeting APC surface determinants.

In order to carry out this study, three mouse monoclonal antibodies, of IgG2a subclass, which all have the capacity for binding ZZ, were selected. The first, called Mα2-3, described in Trémeau et al., FEBS Lett., 1986, 208, 236-240, is used as a control since it does not bind APCs. The other two antibodies are specific for APC surface determinants. The first, called 14-4-4S, recognizes the MHC class II molecule I-E$^d$ (Ozato et al., J. Immunol., 1980, 122, 549). The second, called 10-1.D.2, recognizes the Lyb-2.1 antigen which is expressed at the surface of B lymphocytes (number ATCC TIB-165).

In order to evaluate the T-stimulating capacity of ZZ-DTR in the presence of antibodies, ZZDTR is diluted in the presence or absence of 14-4-4S, 10-1.D.2 and Mα2-3, respectively. The antibodies are incubated at final concentration of 50 nM. Following these dilutions, the compounds are incubated for 3 h at 4° C. and then APCs are added. The APCs are, firstly, A20 cells ($5 \times 10^4$/50 μl/well) and secondly, BALB/c mouse splenocytes ($5 \times 10^5$/50 μl/well). After 2 h at 37° C., the T4B6 hybridoma ($5 \times 10^4$/50 μl/well) is added and the mixture is incubated for 24 h at 37° C. The stimulation of the T4B6 cell is then evaluated by measuring its interleukin-2 secretion. This measurement is carried out on the culture supernatants which are incubated on a CTL line of which the growth is dependent on the presence of IL-2.

As can be seen in FIG. 11, in the presence of A20 cells, ZZDTR-BD stimulates T4B6. Amounts of ZZDTR-BD which are approximately 13.4 times and 3.8 times lower are required to reach the same level of stimulation when the fusion protein is respectively complexed with anti-MHC (anti-MHC/ZZDTR-BD) and with anti-Lyb-2.1 (anti-Lyb-2.1/ZZDTR-BD). The increase in T-stimulating capacity is not due to the fact that anti-MHC and anti-Lyb-2.1 are immunoglobulins of subclass 2a, since the effect is not found when ZZDTR-BD is complexed with an IgG2a not specific for an APC surface determinant (IgG2a/ZZDTR-BD). These results therefore demonstrate that the T-stimulating capacity of ZZDTR-BD is increased by targeting the MHC class II or Lyb-2.1 molecules which are expressed selectively at the surface of the A20 cells used as APCs.

In the presence of splenocytes, ZZDTR-BD stimulates T4B6. Amounts of ZZDTR-BD that are approximately 5.2 times lower are required to reach the same level of stimulation when the fusion protein is complexed with anti-MHC (anti-MHC/ZZDTR-BD). On the other hand, when ZZDTR-BD is complexed with the anti-Lyb-2.1 antibody (anti-Lyb-2.1/ZZDTR-BD), the T-stimulating capacity is slightly decreased. The increase in the T-stimulating capacity mediated by the anti-MHC and also the decrease in T-stimulating capacity mediated by the anti-Lyb-2.1 are not due to the fact that these immunoglobulins are of subclass 2a, since the effect is not found when ZZDTR-BD is complexed with an IgG2a not specific for an APC surface determinant (IgG2a/ZZDTR-BD). These results therefore demonstrate that the T-stimulating capacity of ZZDTR-BD is increased by targeting the MHC class II molecules that are expressed selectively at the surface of splenocytes.

EXAMPLE 7

Two Different Ags which are Respectively Associated with an HS Ligand with an Antibody Capable of Binding an APC Surface Protein Bind, Preferentially and in an Increased Manner, APCs Expressing this Surface Protein Two splenocyte-binding experiments were carried out in order to evaluate whether the Ags which are associated with an HS ligand and with an antibody specific for an APC surface protein are capable of preferentially targeting APCs.

7.1 Splenocyte-binding Study Using the Protein System Described in Example 3

7.1.1 Study of Binding in the Presence or Absence of the Heparan Sulfate Ligand

The wild-type alpha toxin and alpha37-57 toxin were preincubated in the presence or absence of the anti-alpha toxin rabbit polyclonal antibody. The mixtures were then added to splenocytes ($5 \times 10^5$/100 μl/well) and incubated for 30 minutes at 4° C. The cells were washed and incubated in the presence of an anti-rabbit antibody polyclonal antibody coupled to fluorescein. After 30 minutes at 4° C., the cells were washed and the binding of the anti-alpha toxin/alpha toxin and anti-alpha toxin/alpha37-57 toxin complexes was evaluated by flow cytometry.

As can be seen in FIG. 12, the cells incubated in the presence of the anti-rabbit antibody polyclonal antibody coupled to fluorescein exhibit a low level of fluorescence which results in a geometric mean of 3.6. The splenocytes preincubated with the alpha/anti-alpha complex exhibit a medium level of fluorescence which is increased by a factor of 2.75 (geometric mean of 9.9). Finally, the cells preincubated with the alpha37-57/anti-alpha complex exhibit a mixed profile. A first cell population exhibits weak labeling (geometric mean of 4.44) which is not very different than that of the cells incubated in the absence of complex. On the other hand, a second population fluoresces much more strongly (geometric mean of 232.1, intensity multiplied by 64.5-fold). These observations therefore indicate that the alpha37-57/anti-alpha complex has the particularity of binding in increased amount to a subpopulation of splenocytes.

7.1.2 Determination of the Splenocyte Subpopulations Bound by the Anti-alpha Toxin/Alpha37-57 Toxin Complex In order to determine the splenocyte population bound by the anti-alpha toxin/alpha37-57 toxin complex, a fixed amount of this complex (10 nM) was incubated in the presence or absence of splenocytes and of three antibodies respectively specific for CD4+ T lymphocytes (anti-CD4), for CD8+ T lymphocytes (anti-CD8) and for B lymphocytes (anti-CD19). These three antibodies are labeled with phycoerythrin. After 30 minutes at 4° C., the cells were washed and incubated in the presence of an anti-rabbit antibody polyclonal antibody coupled to fluorescein. 30 minutes later, the cells were washed and analyzed by flow cytometry.

As can be seen in FIG. 13, the splenocytes contain approximately 14% CD8+ T lymphocytes, and 6.4% of these cells are bound by the alpha37-57+anti-alpha complex. The splenocytes contain approximately 26% CD4+ T lymphocytes, and 5.5% of these cells are bound by the complex. The splenocytes contain approximately 49% of B lymphocytes and virtually all these cells are bound by the complex. Since B cells bear Fc receptors, whereas CD4+ T and CD8+ T cells are devoid of Fc receptors, it can therefore be concluded therefrom that the alpha37-57/anti-alpha complex binds preferentially and in an increased manner to B lymphocytes, which are Fc receptor-bearing APCs.

7.2 Study of Splenocyte-Binding Using the 14-4-4S/ZZDTR-BD Protein System Described in Example 5

In order to determine the splenocyte population bound by the 14-4-4S/ZZDTR-BD complex, a fixed amount of this complex (10 nM) was incubated in the presence or absence of splenocytes and four antibodies respectively specific for CD4+ T lymphocytes, for CD8+ T lymphocytes, for B lymphocytes and for MHC class II I-Ad and I-Ed molecules. These antibodies are labeled with phycoerythrin. After 30 minutes at 4° C., the cells were washed and incubated in the presence of an anti-rabbit antibody polyclonal antibody coupled to fluorescein. 30 minutes later, the cells were washed and analyzed by flow cytometry.

As can be seen in FIG. 14, ZZDTR-BD interacts weakly with the CD8+ T lymphocytes (approximately 12.4% of the CD8Ts are labeled) and this is also the case for the 14-4-4/ZZDTR-BD complex (approximately 13.3% of the CD8Ts are labeled). ZZDTR-BD interacts weakly with the CD4+ T lymphocytes (approximately 11.7% of the CD8Ts are labeled) and this is also the case for the 14-4-4/ZZDTR-BD complex (approximately 11% of the CD8Ts are labeled). ZZDTR-BD interacts more strongly with the B lymphocytes (approximately 50% of the B lymphocytes are labeled) and this is also the case for the 14-4-4/ZZDTR-BD complex (approximately 68.5% of the CD8Ts are labeled). The targeting antibody therefore makes it possible to increase by 37% the number of B cells bound by ZZDTR-BD. As it happens, B cells are APCs bearing MHC class II molecules. The 14-4-4S/ZZDTR-BD molecular complex therefore preferentially binds to APCs expressing MHC class II molecules.

EXAMPLE 8

A Compound Having the Capacity to Target HSs and a Molecule Expressed Specifically at the Surface of APCs (14-4-4S/ZZDTR-BD) is Capable of Inducing an Immune Response that is Greater than that Induced by a Compound which has the Capacity to Target a Broader Variety of Cells (Mα2-3/ZZDTR-BD)

In order to evaluate whether the targeting of HSs and of a receptor expressed specifically at the surface of APCs is capable of inducing an increased immune response "in vivo", the immunogenicity of ZZDTR-BD when it is complexed with the 14-4-4S antibody, which targets APCs expressing class II molecules, and when it is complexed with a control antibody of the same isotype (IgG2a), was compared.

Before injection, the ZZDTR-BD fusion protein and the two Abs were diluted in HBSS medium. ZZDTR-BD was then incubated for one hour at ambient temperature in the presence of equimolar amounts of the anti-MHC or of the control IgG2a. Two groups of four mice were then injected in the absence of adjuvant (0.01 nmol of complex/mouse/100 µl) with the anti-MHC/ZZDTR-BD complex or with the IgG2a/ZZDTR-BD complex, respectively. Forty-five days after the injection, the blood of the animals was taken and the sera were pooled. The presence of anti-diphtheria toxin antibodies was then evaluated by immunoenzymatic assay using microtitration plates which were adsorbed beforehand with a non-toxic mutant of diphtheria toxin, called CRM197, described by Uchida et al., Science, 1972, 175, 901-903 (0.1 µg of CRM197/well/100 µl PBS). In order to carry out this evaluation, the two pooled sera were respectively diluted and incubated overnight at 4° C. in the microtitration plates. The plates were subsequently washed and then incubated in the presence of a goat anti-mouse IgG antibody coupled to peroxidase. After 30 minutes, the plates were washed, a substrate (ABTS) was added, and the coloration was measured at 414 nm after incubation for a further 30 minutes. On the basis of these measurements, the antibody titers are defined as the serum dilution resulting in an OD of 0.6.

As can be seen in FIG. 15, a titer of 1/3400 is measured for the serum derived from the immunization with the IgG2a/ZZDTR-BD complex, thereby indicating that this complex is capable of inducing an anti-diphtheria toxin antibody response in the absence of adjuvant. This titer is, however, lower than that measured for the serum derived from the immunization with the anti-MHC/ZZDTR-BD complex (1/12 000), thereby indicating that the targeting of the MHC class II molecules makes it possible to increase the humoral immune response induced against the complex.

EXAMPLE 9

A Compound Having the Capacity to Target HSs, a Molecule Expressed Specifically at the Surface of APCs and a CD8+ T Epitope is Capable of Inducing an Immune Response which is Greater than a Compound which Targets Only HSs In order to evaluate whether the double targeting also makes it possible to increase the capacity for stimulating cytotoxic CD8+ T cells, several fusion proteins were constructed. The first fusion protein contains the immunoglobulin-binding ZZ double domain (SEQ ID NO: 3), a CD8+ T epitope of sequence SIINFEKL (SEQ ID NO: 10) which is derived from ovalbumin (the flanking sequences LEQLE (SEQ ID NO: 11) and TEWTS (SEQ ID NO: 12) are respectively inserted at the N-terminal and C-terminal of this epitope), a CD4+ T epitope of sequence SYKKVWRDHRGTI (SEQ ID NO:13), and the Tat22-57$_{C(22-37)S}$ fragment which contains the Tat region capable of binding to heparan sulfates. The second fusion protein contains the immunoglobulin-binding ZZ double domain (SEQ ID NO: 3), a CD8+ T epitope of sequence SIINFEKL (SEQ ID NO: 10) which is derived from ovalbumin (the flanking sequences LEQLE (SEQ ID NO: 11) and TEWTS (SEQ ID NO: 12) are respectively inserted at the N-terminal and C-terminal of this epitope), and a CD4+ T epitope of sequence SYKKVWRDHRGTI (SEQ ID NO: 13). The third fusion protein contains the immunoglobulin-binding ZZ double domain (SEQ ID NO: 3), ovalbumin, and the Tat22-57$_{C(22-37)S}$ fragment which contains the Tat region capable of binding to heparan sulfates. The fourth fusion protein contains the immunoglobulin-binding ZZ double domain and ovalbumin. Ovalbumin is used as a control. These fusion proteins were used free or complexed either with the AF6-120.1 monoclonal antibody specific for the MHC class II I-Ab molecule (#553549; Becton-Dickinson Biosciences), or with a monoclonal antibody which is nonspecific but of the same subclass (IgG2a) as AF6-120.1, or with a rabbit anti-mouse IgG polyclonal antibody, or with a nonspecific rabbit antibody. The formation of the complexes was carried out under conditions identical to those described in the sixth example.

In order to evaluate the stimulating capacity of the various compounds, the B3Z hybridoma which recognizes the T epitope of sequence SIINFEKL in association with class I molecules of type I-Ab was used. Alternatively, splenocytes derived from OT1 mice, which contain CD8+ T cells which also recognize the SIINFEKL epitope, were used. For evaluating the stimulation of the B3Z hybridoma, the fusion proteins (antigens) were incubated in the presence or absence of each of the four antibodies described previously. The mixtures were added to the APCs. The APCs are, firstly, a dendritic cell line (5×104/50 µl/well), and secondly, C57Bl/6 mouse splenocytes (5×105/50 µl/well).

To evaluate the stimulation of the B3Z hybridoma, the antigens (Ags) were incubated for 2 h at 37° C. in the presence of APCs, the B3Z cells (5×10$^4$/50 µl/well) were added and the mixtures were incubated for 24 h at 37° C. The stimulation of the B3Z cell is then evaluated either by measuring interleukin-2 secretion, or by measuring the expression of the Lac Z gene which encodes β-galactosidase. The IL-2 secretion measurement is carried out using the culture supernatants which are subsequently incubated on a CTL line of which the growth is dependent on the presence of IL-2. The measurement of the β-galactosidase activity is carried out using chlorophenolred-β-D-galactopyranoside as substrate.

To evaluate the stimulation of the OT1 cells, the Ags were incubated for 5 h at 37° C. in the presence of JAWS II dendritic cells. The cells were then fixed with glutaraldehyde and then OT1 mouse splenocytes (5×10$^5$/50 µl/well) were added and the mixtures were incubated for 3 days at 37° C. Tritiated thymidine was then added (1 µCi/well). After incubation for 18 hours at 37° C., the cells were removed and the radioactivity incorporated into the cells was measured in order to evaluate the OT1 cell proliferation.

EXAMPLE 10

A Compound Having the Capacity to Target HSs, a Molecule Expressed Specifically at the Surface of APCs and an Ag is Capable of Inducing a Greater Immune Response "In Vivo" than a Compound which Contains the Same Ag but Targets Only the Molecule Expressed Specifically at the Surface of APCs In order to evaluate whether the double targeting also makes it possible to increase the immune response "in vivo", several fusion proteins were constructed. The first fusion protein contains the immunoglobulin-binding ZZ double domain (SEQ ID NO: 3), a CD8+ T epitope of sequence SIINFEKL (SEQ ID NO: 10) which is derived from ovalbumin (the flanking sequences LEQLE (SEQ ID NO: 11) and TEWTS (SEQ ID NO: 12) are respectively inserted at the N-terminal and C-terminal of this epitope), a CD4+ T epitope of sequence SYKKVWRDHRGTI (SEQ ID NO: 13), and the Tat22-57$_{C(22-37)S}$ fragment which contains the Tat region capable of binding to heparan sulfates. The second fusion protein contains the immunoglobulin-binding ZZ double domain (SEQ ID NO: 3), a CD8+ T epitope of sequence SIINFEKL (SEQ ID NO: 10) which is derived from ovalbumin (the flanking sequences LEQLE (SEQ ID NO: 11) and TEWTS (SEQ ID NO: 12) are respectively inserted at the N-terminal and C-terminal of this epitope), and a CD4+ T epitope of sequence SYKKVWRDHRGTI (SEQ ID NO: 13). The third fusion protein contains the immunoglobulin-binding ZZ double domain (SEQ ID NO: 3), ovalbumin, and the Tat22-57$_{C(22-37)S}$ fragment which contains the Tat region capable of binding to heparan sulfates. The fourth fusion protein contains the immunoglobulin-binding ZZ double domain (SEQ ID NO: 3) and ovalbumin. Ovalbumin is used as a control. These fusion proteins were used free or complexed either with the AF6-120.1 monoclonal antibody specific for the MHC class II I-Ab molecule (#553549; Becton-Dickinson Biosciences), or with a monoclonal antibody which is nonspecific but of the same subclass (IgG2a) as AF6-120.1, or with a rabbit anti-mouse IgG polyclonal antibody, or with a nonspecific rabbit antibody. The formation of the complexes was carried out under conditions identical to those described in the sixth example.

In order to evaluate the immune response in animals, the various mixtures were injected, in the presence or absence of adjuvant, into mice (6 animals per group). Fourteen days after the second immunization, a blood sample was taken from the animals in order to evaluate the humoral response. The animals were then sacrificed and their spleen was removed in order to evaluate the cellular response. The humoral response was evaluated by immunoenzymatic assay of the anti-ovalbumin antibodies. In order to evaluate the cellular response, the presence of specific T lymphocytes was determined by counting cells secreting interferon gamma or IL-4 using an ELISPOT assay according to the protocol described in Turbant et al., Vaccine, 2009, 27, 5349-56.

EXAMPLE 11

A Compound Having the Capacity to Target HCs and a Molecule Expressed Specifically at the Surface of APCs is Capable of Inducing a Greater Cytotoxic Immune Response than a Compound which Targets Only HSs or Only the Molecule Expressed Specifically at the Surface of APCs In order to evaluate whether the double targeting makes it possible to increase the capacity for stimulating cytotoxic CD8+ T cells, two chimeric proteins were chemically synthesized. The first protein, called Tat47-57-SIINFEKL-alpha, contains the sequence of the alpha toxin from *Naja nigricollis* (SEQ ID NO: 9), a CD8+ T epitope of sequence SIINFEKL (SEQ ID NO: 10) which is derived from ovalbumin (the flanking sequences LEQLE (SEQ ID NO: 11) and TEWTS (SEQ ID NO: 12) are respectively inserted at the N-terminal and C-terminal of this epitope), and the Tat47-57 fragment (SEQ ID NO: 14) which contains the Tat region capable of binding to heparan sulfates. The second protein, called SIINFEKL-alpha, contains the sequence of the alpha toxin from *Naja nigricollis* (SEQ ID NO: 9), and a CD8+ T epitope of sequence SIINFEKL (SEQ ID NO: 10) which is derived from ovalbumin (the flanking sequences LEQLE (SEQ ID NO: 11) and TEWTS (SEQ ID NO: 12) are respectively inserted at the N-terminal and C-terminal of this epitope). These two proteins were used free or complexed with the rabbit anti-alpha toxic polyclonal antibody, called anti-alpha, described in example 3. The formation of the complexes was carried out by incubation overnight at 4° C.

In order to evaluate the stimulating capacity of the two compounds, OT1 mouse splenocytes were used. These splenocytes contain CD8+ T lymphocytes which recognize the T epitope of sequence SIINFEKL, in association with class I molecules of type I-A$^b$. The two proteins (final dilution 1 μM) complexed or not complexed with the antibody (50 nM) were respectively incubated in cell culture plates in the presence of a dendritic cell line used as APCs. This line, called JAWS II, was incubated in a proportion of 3×10$^4$/50 μl/well. After 5 h at 37° C., the plates were washed and the cells were fixed with glutaraldehyde. After fixing, OT1 mouse splenocytes were added (9×10$^4$/50 μl/well). After incubation for 4 days at 37° C., a solution of tritiated thymidine was added (1 μCi/25 μl/well) and the plates were incubated for 18 hours at 37° C. The cells were then removed and the radioactivity was measured in order to evaluate cell proliferation. As can be seen in FIG. 16, the free SIINFEKL-alpha compound is capable of inducing CD8+ T-cell proliferation. In the presence of a fixed concentration of anti-alpha (50 nM final concentration), SIINFEKL-alpha stimulates OT1 cells more strongly, thereby indicating that the Fcγ-receptor-mediated targeting also makes it possible to increase cross-presentation, as had been observed previously for other antigens (Regnault, J. Exp. Med., 1999, 371-380). An increase in the stimulation of OT1 cells is also observed for the Tat47-57-SIINFEKL-alpha compound, thereby indicating that the targeting mediated by binding to HSs makes it possible to increase cross-presentation. The greatest increase in OT1 cell stimulation is, however, observed when Tat47-57-SIINFEKL-alpha is complexed with the anti-alpha antibody, thereby indicating that the targeting mediated jointly by HSs and Fc receptors provides a synergistic effect on cross-presentation of the antigenic protein.

EXAMPLE 12

A Compound Having the Capacity to Target HSs and a Molecule Expressed Specifically at the Surface of APCs Increases More Strongly the Expression of the Costimulatory Molecules of CD80 and CD86 than Compounds which Target Only HSs or Only the Molecule Expressed Specifically at the Surface of APCs Antigen-presenting capacity represents an essential aspect in setting up an adaptive immune response. However, the setting up of this response also requires the activation of antigen-presenting cells (APCs). For this reason, the capacity of the molecular targeting complexes to activate APCs was evaluated. In order to evaluate this aspect, the ability of the molecular targeting complex described in example 11 to increase the expression of the costimulatory molecules CD80 and CD86 by JAWS II APCs, described previously, was analyzed. The chimeric proteins and antibodies used to carry out this evaluation are those described in example 11. The two proteins were used free or complexed with the rabbit anti-alpha toxin polyclonal antibody. The formation of the complexes was carried out by incubation overnight at 4° C. The wild-type alpha toxin was also used, as a control.

The two proteins (1 μM final concentration), complexed or not complexed with the antibody (25 nM final concentration), were respectively diluted and incubated in cell culture plates in the presence of the JAWS II line (5×10$^5$/100 μl/well) for 24 hours at 37° C. The cells were then washed and incubated for 30 minutes at 4° C. in the presence of anti-CD80 antibody labeled with fluorescein and anti-CD86 antibody labeled with fluorescein, respectively. Finally, the antibody binding to the cells was analyzed by flow cytometry. As can be seen in FIG. 17A, when the cells were incubated in the presence of SIINFEKL-alpha, the CD80 molecule is expressed at the surface of the APCs. The expression of the CD80 molecule is increased when the JAWS II were incubated with Tat47-57-SIINFEKL-alpha or with the SIINFEKL-alpha/anti-alpha complex. However, the expression of CD80 is more strongly increased for the Tat47-57-SIINFEKL-alpha/anti-alpha complex, thereby indicating that the molecular targeting complex provides a synergistic effect. The same behavior is observed for the CD86 molecule (cf. FIG. 17B). Thus, when the cells were incubated in the presence of SIINFEKL-alpha, the CD86 molecule is expressed at the surface of the APCs. The expression of the CD86 molecule is increased when the JAWS II were incubated with Tat47-57-SIINFEKL-alpha or with the SIINFEKL-alpha/anti-alpha complex. However, the expression of CD86 is more strongly increased for the Tat47-57-SIINFEKL-alpha/anti-alpha complex, thereby indicating that the molecular targeting complex provides a synergistic effect.

This example, which demonstrates the synergistic effect on the expression of the costimulatory molecules CD80 and CD86, therefore indicates that the molecular targeting complex brings about activation of Ag-presenting cells.

The invention claimed is:

1. An isolated immunogenic complex comprising at least one antigen associated with at least two protein or peptide ligands of surface molecules of antigen-presenting cells, said at least two protein or peptide ligands at least one first ligand of heparan sulfates and one second ligand of a surface molecule specific for antigen-presenting cells, wherein the first ligand is an isolated peptide consisting of the R domain of diphtheria toxin (SEQ ID NO: 6);

the second ligand is selected from the group consisting of: a BB fragment of *Staphylococcus aureus* protein A (SEQ ID NO: 4) and a ZZ derivative thereof (SEQ ID NO: 3), said antigen is a protein or a peptide which is specific for a tumor, said first ligand is covalently bonded to said antigen and to said second ligand, said complex does not comprise the full length diphtheria toxin, and said complex induces an anti-tumor immune response.

2. The immunogenic complex of claim 1, wherein said second ligand is the BB fragment (SEQ ID NO: 4).

3. An immunogenic or vaccine composition, comprising at least one immunogenic complex of claim 1, and a pharmaceutically acceptable vehicle.

4. The immunogenic or vaccine composition of claim 3, comprising an amount of said complex sufficient to reduce tumor growth.

5. The immunogenic complex of claim 1, which comprises an amount of said antigen sufficient to treat cancer.

6. The immunogenic complex of claim 1, wherein the second ligand is the ZZ derivative thereof (SEQ ID NO: 3).

* * * * *